United States Patent

Carrison et al.

(10) Patent No.: US 9,131,941 B2
(45) Date of Patent: Sep. 15, 2015

(54) FISTULA TREATMENT DEVICES AND METHODS

(75) Inventors: Harold F. Carrison, Pleasanton, CA (US); Mark-Christopher O. Santos, San Diego, CA (US)

(73) Assignee: CURASEAL INC., Santa Clara, CA (US)

( * ) Notice: Subject to any disclaimer, the term of this patent is extended or adjusted under 35 U.S.C. 154(b) by 432 days.

(21) Appl. No.: 13/525,081

(22) Filed: Jun. 15, 2012

(65) Prior Publication Data

US 2013/0158594 A1 Jun. 20, 2013

Related U.S. Application Data

(60) Provisional application No. 61/498,449, filed on Jun. 17, 2011.

(51) Int. Cl.
| | |
|---|---|
| *A61B 17/08* | (2006.01) |
| *A61D 1/00* | (2006.01) |
| *A61B 17/04* | (2006.01) |
| *A61B 17/00* | (2006.01) |

(52) U.S. Cl.
CPC ............. *A61B 17/08* (2013.01); *A61B 17/0401* (2013.01); *A61B 17/0469* (2013.01); *A61B 2017/00641* (2013.01); *A61B 2017/0404* (2013.01); *A61B 2017/0417* (2013.01)

(58) Field of Classification Search
CPC ..................... A61B 17/0057; A61B 17/12022; A61B 2017/00641
USPC ................. 606/191, 194, 198, 200, 213, 214; 623/11.11, 23.64
See application file for complete search history.

(56) References Cited

U.S. PATENT DOCUMENTS

| | | | |
|---|---|---|---|
| 2,324,520 | A | 7/1943 | Lamson |
| 2,510,766 | A | 6/1950 | Surface |
| 2,564,399 | A | 8/1951 | Franken |

(Continued)

FOREIGN PATENT DOCUMENTS

| | | |
|---|---|---|
| DE | 2637119 A1 | 3/1977 |
| EP | 1985247 A1 | 10/2008 |

(Continued)

OTHER PUBLICATIONS

Supplementary European Search Report issued by the European Patent Office for Application No. 12801043.6, Jan. 15, 2015, 1-7.

(Continued)

*Primary Examiner* — Katherine M Shi
(74) *Attorney, Agent, or Firm* — Dorsey & Whitney LLP

(57) ABSTRACT

Disclosed herein are implantable fistula treatment devices and related methods. In some embodiments, an anorectal fistula treatment device may comprise a disc-shaped distal anchor comprising a concave side and a convex side, an outer edge region, an inner sealing region protruding from the concave side, and an attachment region configured for attachment to a connecting member. The inner sealing region may have a greater thickness than at least a portion of the attachment region and the outer edge region may be oriented at an acute angle to the inner sealing region. The distal anchor may have a tapered edge and the outer edge region and inner sealing region may be configured to form separate seals against tissue about a distal opening of an anorectal fistula.

28 Claims, 12 Drawing Sheets

(56) References Cited

U.S. PATENT DOCUMENTS

| | | | |
|---|---|---|---|
| 2,934,068 | A | 4/1960 | Graham, Jr. et al. |
| 3,447,533 | A | 6/1969 | Spicer |
| 3,882,858 | A | 5/1975 | Klemm |
| 4,057,535 | A | 11/1977 | Lipatova et al. |
| 4,241,735 | A | 12/1980 | Chernov |
| 4,365,621 | A | 12/1982 | Brundin |
| 4,390,018 | A | 6/1983 | Zukowski |
| 4,532,926 | A | 8/1985 | O'Holla |
| 4,669,473 | A | 6/1987 | Richards et al. |
| 4,705,040 | A | 11/1987 | Mueller et al. |
| 4,744,364 | A | 5/1988 | Kensey |
| 4,795,438 | A | 1/1989 | Kensey et al. |
| 4,836,204 | A | 6/1989 | Landymore et al. |
| 4,852,568 | A | 8/1989 | Kensey |
| 4,890,612 | A | 1/1990 | Kensey |
| 4,917,089 | A | 4/1990 | Sideris |
| 4,935,028 | A | 6/1990 | Drews |
| 4,983,177 | A | 1/1991 | Wolf |
| 5,021,059 | A | 6/1991 | Kensey et al. |
| 5,053,046 | A | 10/1991 | Janese |
| 5,061,274 | A | 10/1991 | Kensey |
| 5,108,421 | A | 4/1992 | Fowler |
| 5,122,136 | A | 6/1992 | Guglielmi et al. |
| 5,192,301 | A | 3/1993 | Kamiya et al. |
| 5,192,302 | A | 3/1993 | Kensey et al. |
| 5,222,974 | A | 6/1993 | Kensey et al. |
| 5,242,456 | A | 9/1993 | Nash et al. |
| 5,258,042 | A | 11/1993 | Mehta |
| 5,282,827 | A | 2/1994 | Kensey et al. |
| 5,306,254 | A | 4/1994 | Nash et al. |
| 5,312,435 | A | 5/1994 | Nash et al. |
| 5,334,217 | A | 8/1994 | Das |
| 5,350,399 | A | 9/1994 | Erlebacher et al. |
| 5,354,295 | A | 10/1994 | Guglielmi et al. |
| 5,370,660 | A | 12/1994 | Weinstein et al. |
| 5,374,261 | A | 12/1994 | Yoon et al. |
| RE34,866 | E | 2/1995 | Kensey et al. |
| 5,391,183 | A | 2/1995 | Janzen et al. |
| 5,411,520 | A | 5/1995 | Nash et al. |
| 5,433,727 | A | 7/1995 | Sideris |
| 5,441,517 | A | 8/1995 | Kensey et al. |
| 5,522,836 | A | 6/1996 | Palermo |
| 5,531,757 | A | 7/1996 | Kensey et al. |
| 5,531,759 | A | 7/1996 | Kensey et al. |
| 5,540,680 | A | 7/1996 | Guglielmi et al. |
| 5,545,178 | A | 8/1996 | Kensey et al. |
| 5,549,633 | A | 8/1996 | Evans et al. |
| 5,582,619 | A | 12/1996 | Ken |
| 5,591,204 | A | 1/1997 | Janzen et al. |
| 5,593,422 | A | 1/1997 | Muijs van de Moer et al. |
| 5,609,628 | A | 3/1997 | Keranen |
| 5,620,461 | A | 4/1997 | Muijs van de Moer et al. |
| 5,624,449 | A | 4/1997 | Pham et al. |
| 5,643,254 | A | 7/1997 | Scheldrup et al. |
| 5,645,558 | A | 7/1997 | Horton |
| 5,649,949 | A | 7/1997 | Wallace et al. |
| 5,662,681 | A | 9/1997 | Nash et al. |
| 5,669,905 | A | 9/1997 | Scheldrup et al. |
| 5,676,689 | A | 10/1997 | Kensey et al. |
| 5,681,334 | A | 10/1997 | Evans et al. |
| 5,700,277 | A | 12/1997 | Nash et al. |
| 5,707,393 | A | 1/1998 | Kensey et al. |
| 5,713,891 | A | 2/1998 | Poppas |
| 5,725,552 | A | 3/1998 | Kotula et al. |
| 5,743,905 | A | 4/1998 | Eder et al. |
| 5,749,891 | A | 5/1998 | Ken et al. |
| 5,752,974 | A | 5/1998 | Rhee et al. |
| 5,766,219 | A | 6/1998 | Horton |
| 5,782,860 | A | 7/1998 | Epstein et al. |
| 5,785,679 | A | 7/1998 | Abolfathi et al. |
| 5,810,884 | A | 9/1998 | Kim |
| 5,824,054 | A | 10/1998 | Khosravi et al. |
| 5,833,705 | A | 11/1998 | Ken et al. |
| 5,853,418 | A | 12/1998 | Ken et al. |
| 5,855,578 | A | 1/1999 | Guglielmi et al. |
| 5,861,004 | A | 1/1999 | Kensey et al. |
| 5,879,366 | A | 3/1999 | Shaw et al. |
| 5,904,703 | A | 5/1999 | Gilson |
| 5,911,731 | A | 6/1999 | Pham et al. |
| 5,916,236 | A | 6/1999 | Muijs van de Moer et al. |
| 5,925,037 | A | 7/1999 | Guglielmi et al. |
| 5,928,226 | A | 7/1999 | Guglielmi et al. |
| 5,935,145 | A | 8/1999 | Villar et al. |
| 5,935,147 | A | 8/1999 | Kensey et al. |
| 5,944,714 | A | 8/1999 | Guglielmi et al. |
| 5,947,962 | A | 9/1999 | Guglielmi et al. |
| 5,957,900 | A | 9/1999 | Ouchi |
| 5,957,948 | A | 9/1999 | Mariant |
| 5,976,126 | A | 11/1999 | Guglielmi |
| 5,989,281 | A | 11/1999 | Barbut et al. |
| 5,990,379 | A | 11/1999 | Gregory |
| 6,004,338 | A | 12/1999 | Ken et al. |
| 6,007,563 | A | 12/1999 | Nash et al. |
| 6,010,498 | A | 1/2000 | Guglielmi |
| 6,010,517 | A | 1/2000 | Baccaro |
| 6,013,084 | A | 1/2000 | Ken et al. |
| 6,033,423 | A | 3/2000 | Ken et al. |
| 6,045,569 | A | 4/2000 | Kensey et al. |
| 6,045,570 | A | 4/2000 | Epstein et al. |
| 6,056,768 | A | 5/2000 | Cates et al. |
| 6,063,100 | A | 5/2000 | Diaz et al. |
| 6,066,133 | A | 5/2000 | Guglielmi et al. |
| 6,077,260 | A | 6/2000 | Wheelock et al. |
| 6,080,183 | A | 6/2000 | Tsugita et al. |
| 6,083,220 | A | 7/2000 | Guglielmi et al. |
| 6,087,552 | A | 7/2000 | Gregory |
| 6,090,125 | A | 7/2000 | Horton |
| 6,090,130 | A | 7/2000 | Nash et al. |
| 6,171,326 | B1 | 1/2001 | Ferrera et al. |
| 6,179,857 | B1 | 1/2001 | Diaz et al. |
| 6,179,863 | B1 | 1/2001 | Kensey et al. |
| 6,183,491 | B1 | 2/2001 | Lulo |
| 6,187,027 | B1 | 2/2001 | Mariant et al. |
| 6,190,400 | B1 | 2/2001 | Van de Moer et al. |
| 6,203,563 | B1 | 3/2001 | Fernandez |
| 6,231,562 | B1 | 5/2001 | Khosravi et al. |
| 6,238,403 | B1 | 5/2001 | Greene et al. |
| 6,270,495 | B1 | 8/2001 | Palermo |
| 6,287,318 | B1 | 9/2001 | Villar et al. |
| 6,296,658 | B1 | 10/2001 | Gershony et al. |
| 6,306,153 | B1 | 10/2001 | Kurz et al. |
| 6,315,787 | B1 | 11/2001 | Tsugita et al. |
| 6,371,972 | B1 | 4/2002 | Wallace et al. |
| 6,383,204 | B1 | 5/2002 | Ferrera |
| 6,409,721 | B1 | 6/2002 | Wheelock et al. |
| 6,454,780 | B1 | 9/2002 | Wallace |
| 6,476,069 | B2 | 11/2002 | Krall et al. |
| 6,503,527 | B1 | 1/2003 | Whitmore et al. |
| 6,538,026 | B1 | 3/2003 | Krall et al. |
| 6,551,303 | B1 | 4/2003 | Van Tassel et al. |
| 6,551,305 | B2 | 4/2003 | Ferrera et al. |
| 6,551,340 | B1 | 4/2003 | Konya et al. |
| 6,565,601 | B2 | 5/2003 | Wallace et al. |
| 6,589,230 | B2 | 7/2003 | Gia et al. |
| 6,589,236 | B2 | 7/2003 | Wheelock et al. |
| 6,592,566 | B2 | 7/2003 | Kipke et al. |
| 6,599,308 | B2 | 7/2003 | Amplatz |
| 6,605,101 | B1 | 8/2003 | Schaefer et al. |
| 6,613,037 | B2 | 9/2003 | Khosravi et al. |
| 6,623,493 | B2 | 9/2003 | Wallace et al. |
| 6,623,508 | B2 | 9/2003 | Shaw et al. |
| 6,635,069 | B1 | 10/2003 | Teoh et al. |
| 6,638,291 | B1 | 10/2003 | Ferrera et al. |
| 6,656,173 | B1 | 12/2003 | Palermo |
| 6,656,201 | B2 | 12/2003 | Ferrera et al. |
| 6,656,206 | B2 | 12/2003 | Corcoran et al. |
| 6,660,020 | B2 | 12/2003 | Wallace et al. |
| 6,676,971 | B2 | 1/2004 | Goupil et al. |
| 6,682,546 | B2 | 1/2004 | Amplatz |
| 6,699,484 | B2 | 3/2004 | Whitmore et al. |
| 6,723,108 | B1 | 4/2004 | Jones et al. |
| 6,730,108 | B2 | 5/2004 | Van Tassel et al. |
| 6,764,500 | B1 | 7/2004 | Muijs van de Moer et al. |
| 6,790,218 | B2 | 9/2004 | Jayaraman |

(56) References Cited

U.S. PATENT DOCUMENTS

| | | | |
|---|---|---|---|
| 6,872,218 B2 | 3/2005 | Ferrera et al. |
| 6,921,410 B2 | 7/2005 | Porter |
| 6,949,113 B2 | 9/2005 | van Tassel et al. |
| 6,953,468 B2 | 10/2005 | Jones et al. |
| 6,974,862 B2 | 12/2005 | Ringeisen et al. |
| 6,979,344 B2 | 12/2005 | Jones et al. |
| 6,994,717 B2 | 2/2006 | Konya et al. |
| 6,997,918 B2 | 2/2006 | Soltesz et al. |
| 7,011,677 B2 | 3/2006 | Wallace et al. |
| 7,033,348 B2 | 4/2006 | Alfano et al. |
| 7,049,348 B2 | 5/2006 | Evans et al. |
| 7,070,608 B2 | 7/2006 | Kurz et al. |
| 7,166,133 B2 | 1/2007 | Evans et al. |
| 7,169,168 B2 | 1/2007 | Muijs van de Moer et al. |
| 7,179,276 B2 | 2/2007 | Barry et al. |
| 7,182,774 B2 | 2/2007 | Barry et al. |
| 7,214,765 B2 | 5/2007 | Ringeisen et al. |
| 7,294,123 B2 | 11/2007 | Jones et al. |
| 7,316,701 B2 | 1/2008 | Ferrera et al. |
| 7,323,000 B2 | 1/2008 | Monstdt et al. |
| 7,326,225 B2 | 2/2008 | Ferrera et al. |
| 7,331,981 B2 | 2/2008 | Cates et al. |
| 7,485,087 B2 | 2/2009 | Burgard |
| 7,491,214 B2 | 2/2009 | Greene, Jr. et al. |
| 7,601,165 B2 | 10/2009 | Stone |
| 7,682,400 B2 | 3/2010 | Zwirkoski |
| 7,819,898 B2 | 10/2010 | Stone et al. |
| 7,931,671 B2 | 4/2011 | Tenerz |
| 7,998,154 B2 | 8/2011 | Manzo |
| 8,177,809 B2 | 5/2012 | Mavani et al. |
| 8,206,416 B2 | 6/2012 | Mavani et al. |
| 8,221,451 B2 | 7/2012 | Mavani et al. |
| 8,377,094 B2 | 2/2013 | Mavani et al. |
| 2002/0026210 A1 | 2/2002 | Abdel-Gawwad |
| 2002/0058960 A1 | 5/2002 | Hudson et al. |
| 2002/0147457 A1 | 10/2002 | Rousseau |
| 2003/0100920 A1 | 5/2003 | Akin et al. |
| 2003/0220666 A1 | 11/2003 | Mirigian et al. |
| 2004/0034366 A1 | 2/2004 | van der Burg et al. |
| 2004/0044357 A1 | 3/2004 | Gannoe et al. |
| 2004/0044358 A1 | 3/2004 | Khosravi et al. |
| 2004/0044391 A1 | 3/2004 | Porter |
| 2004/0122456 A1 | 6/2004 | Saadat et al. |
| 2004/0186464 A1 | 9/2004 | Mamayek et al. |
| 2004/0199175 A1 | 10/2004 | Jaeger et al. |
| 2004/0225183 A1 | 11/2004 | Michlitsch et al. |
| 2004/0236344 A1 | 11/2004 | Monstadt et al. |
| 2004/0236348 A1 | 11/2004 | Diaz et al. |
| 2004/0237970 A1 | 12/2004 | Vournakis et al. |
| 2005/0033401 A1 | 2/2005 | Cunniffe et al. |
| 2005/0049626 A1 | 3/2005 | Burgard |
| 2005/0049628 A1 | 3/2005 | Schweikert et al. |
| 2005/0070759 A1 | 3/2005 | Armstrong |
| 2005/0090860 A1 | 4/2005 | Paprocki |
| 2005/0090861 A1 | 4/2005 | Porter |
| 2005/0113858 A1 | 5/2005 | Deutsch |
| 2005/0155608 A1 | 7/2005 | Pavcnik et al. |
| 2005/0159776 A1 | 7/2005 | Armstrong |
| 2005/0182495 A1 | 8/2005 | Perrone |
| 2005/0228448 A1 | 10/2005 | Li |
| 2005/0240216 A1 | 10/2005 | Jones et al. |
| 2005/0251200 A1 | 11/2005 | Porter |
| 2005/0267528 A1 | 12/2005 | Ginn et al. |
| 2005/0277981 A1 | 12/2005 | Maahs et al. |
| 2005/0283187 A1* | 12/2005 | Longson ............... 606/213 |
| 2006/0009797 A1 | 1/2006 | Armstrong |
| 2006/0036282 A1 | 2/2006 | Wahr et al. |
| 2006/0052822 A1 | 3/2006 | Mirizzi et al. |
| 2006/0058834 A1 | 3/2006 | Do et al. |
| 2006/0074447 A2 | 4/2006 | Armstrong |
| 2006/0079929 A1 | 4/2006 | Marks et al. |
| 2006/0122633 A1 | 6/2006 | To et al. |
| 2006/0142797 A1 | 6/2006 | Egnelov |
| 2006/0155303 A1 | 7/2006 | Konya et al. |
| 2006/0200192 A1 | 9/2006 | Fitz et al. |
| 2006/0206140 A1 | 9/2006 | Shaolian et al. |
| 2006/0206196 A1 | 9/2006 | Porter |
| 2006/0212055 A1 | 9/2006 | Karabey et al. |
| 2006/0241687 A1 | 10/2006 | Glaser et al. |
| 2006/0264698 A1 | 11/2006 | Kondonis et al. |
| 2006/0265001 A1 | 11/2006 | Marks et al. |
| 2006/0271099 A1 | 11/2006 | Marks et al. |
| 2006/0282112 A1 | 12/2006 | Griffin |
| 2007/0031508 A1 | 2/2007 | Armstrong et al. |
| 2007/0083226 A1 | 4/2007 | Buiser et al. |
| 2007/0088445 A1 | 4/2007 | Patel et al. |
| 2007/0129757 A1 | 6/2007 | Armstrong |
| 2007/0135842 A1 | 6/2007 | Van de Moer et al. |
| 2007/0142859 A1 | 6/2007 | Buiser et al. |
| 2007/0179507 A1 | 8/2007 | Shah |
| 2007/0179527 A1 | 8/2007 | Eskuri et al. |
| 2007/0185530 A1 | 8/2007 | Chin-Chen et al. |
| 2007/0198059 A1 | 8/2007 | Patel et al. |
| 2007/0233278 A1 | 10/2007 | Armstrong |
| 2007/0244502 A1 | 10/2007 | Deutsch |
| 2007/0276121 A1 | 11/2007 | Westergom et al. |
| 2008/0004657 A1 | 1/2008 | Obermiller et al. |
| 2008/0009781 A1 | 1/2008 | Anwar et al. |
| 2008/0015635 A1 | 1/2008 | Olsen et al. |
| 2008/0015636 A1 | 1/2008 | Olsen et al. |
| 2008/0027477 A1 | 1/2008 | Obermiller et al. |
| 2008/0039547 A1 | 2/2008 | Khatri et al. |
| 2008/0039548 A1 | 2/2008 | Zavatsky et al. |
| 2008/0051824 A1 | 2/2008 | Gertner |
| 2008/0051831 A1 | 2/2008 | Deal et al. |
| 2008/0071310 A1 | 3/2008 | Hoffman et al. |
| 2008/0245374 A1 | 10/2008 | Agnew |
| 2009/0054927 A1 | 2/2009 | Agnew |
| 2009/0099647 A1* | 4/2009 | Glimsdale et al. ............ 623/1.35 |
| 2009/0281557 A1 | 11/2009 | Sander et al. |
| 2010/0076463 A1* | 3/2010 | Mavani et al. ................ 606/151 |
| 2010/0087854 A1 | 4/2010 | Stopek et al. |
| 2010/0185234 A1 | 7/2010 | Fortson et al. |
| 2011/0130769 A1* | 6/2011 | Boebel et al. ................. 606/119 |
| 2011/0282368 A1 | 11/2011 | Swayze et al. |
| 2012/0016412 A1 | 1/2012 | Mavani et al. |
| 2012/0035644 A1 | 2/2012 | Eskaros et al. |
| 2012/0059398 A1 | 3/2012 | Pate et al. |
| 2012/0116447 A1 | 5/2012 | Stanley et al. |
| 2012/0323271 A1 | 12/2012 | Obermiller et al. |
| 2013/0006283 A1 | 1/2013 | Carrison et al. |

FOREIGN PATENT DOCUMENTS

| | | |
|---|---|---|
| JP | 2008-543504 | 12/2008 |
| WO | 89/11301 | 11/1989 |
| WO | 00/74576 | 12/2000 |
| WO | 2004/112864 | 12/2004 |
| WO | 2005/070302 | 8/2005 |
| WO | 2006/119256 | 11/2006 |
| WO | 2006/119256 A2 | 11/2006 |
| WO | 2006/130213 | 12/2006 |
| WO | 2007/002260 | 1/2007 |
| WO | 2007/002260 A2 | 1/2007 |
| WO | 2008/112740 | 9/2008 |
| WO | 2009/124148 | 4/2009 |
| WO | 2009124144 | 4/2009 |
| WO | 2009/146369 A1 | 12/2009 |
| WO | 2010/028300 | 3/2010 |
| WO | 2012/050836 | 4/2012 |
| WO | 2012/050836 A1 | 4/2012 |
| WO | 2012/174468 A1 | 12/2012 |
| WO | 2012/174469 A2 | 12/2012 |

OTHER PUBLICATIONS

International Search Report, Issued by the US Searching Authority in PCT Application Serial No. PCT/US14/043261, Dec. 23, 2014, 1-4.
Extended European Search Report issued by the European Patent Office for Application No. 12800217.7, Mar. 24, 2015, 1-6.
Written Opinion of the International Searching Authority Issued by the US Searching Authority in PCT Application Serial No. PCT/US14/043261, Dec. 23, 2014, 1-6.

(56) References Cited

OTHER PUBLICATIONS

"Controlled Deployment for Confident Closure," Angio-Seal Envolution, St. Jude Medical, 2009, pp. 1-3, online publication.

"Datascope's VasoSeal seen as cost effective aid to coronary patients,"Health Industry Today, Copyright Gale, Cengage Learning, 2008, pp. 1-3, online publication.

International Search Report for International Patent Application No. PCT/US2012/042805, mailed Nov. 28, 2012, 5 pages.

Partial International Search Report for International Patent Application No. PCT/US2014/011663, mailed May 9, 2014, 3 pages.

Patent Examination Report No. 1 for Australian Patent Application No. 2009289474, mailed Dec. 11, 2014, 5 pages.

"Practice Parameters for Treatment of Fistula-in-Ano," ASCRS Standards Practice Task Force, Dis Colon Rectum, Dec. 1996, pp. 1361-1362.

International Preliminary Report on Patentability for International Patent.Application No. PCT/US2009/039203, mailed Jul. 14, 2009, 7 pages.

International Preliminary Report on Patentability for International Patent Application No. PCT/US2009/039209, mailed May 27, 2009, 6 pages.

Written Opinion of the International Searching Authority for International Patent Application No. PCT/US2009/056114, mailed Oct. 21, 2009, 11 pages.

Written Opinion of the International Searching Authority for International Patent Application No. PCT/US2009/039209, mailed May 27, 2009, 5 pages.

Written Opinion of the International Searching Authority for International Patent Application No. PCT/US2009/039203, mailed on Jul. 14, 2009, 6 pages.

European Search Report for European Patent Application No. 09728360.0, Apr. 4, 2011, 5 pages.

International Preliminary Report on Patentability for International Patent Application No. PCT/US2009/056114, mailed Oct. 21, 2009, 12 pages.

International Search Report for International Patent Application No. PCT/US2009/039203, mailed Jul. 14, 2009, 3 pages.

International Search Report for International Patent Application No. PCT/US2009/039209, mailed May 27, 2009, 2 pages.

International Search Report for International Patent Application No. PCT/US2009/056114, mailed Oct. 21, 2009, 2 pages.

International Search Report for International Patent Application No. PCT/US14/043280, mailed Nov. 17, 2014, 7 pages.

Written Opinion of the International Searching Authority for International Patent Application No. PCT/US14/043280, mailed Nov. 17, 2014, 9 pages.

Written Opinion of the International Searching Authority for International Patent Application No. PCT/US2012/042805, mailed Nov. 28, 2012, 6 pages.

Champagne et al., "Efficacy of Anal Fistula Plug in Closure of Cryptoglandular Fistulas: Long-Term Follow-Up," Diseases of the Colon & Rectum, Dis. Colon Rectum, Dec. 2006, pp. 1817-1821, vol. 49, No. 12, Georgia.

Draus, Jr. et al., "Enterocutaneous fistula: Are treatments improving?,"Surgery, Oct. 2006, pp. 570-578, vol. 140, No. 4, Kentucky.

Farsi et al., "A new conservative approach in the treatment of post-operative digestive-tract fistulas. Mechanical closure by a balloon-catheter," Minerva Chir., Feb. 2001, full article in Italian, 1 page translation, 56(1):31-9, Italy.

Hollington et al., "An 11-year experience of enterocutaneous fistula," British Journal of Surgery 2004; 91: pp. 1646-1651.

Hyman, "Anorectal Abscess and Fistula," Primary Care: Clinics in Office Practice, Mar. 1999, pp. 69-80, vol. 26, Issue 1.

Jenkins et al.,"Single Operator Deployment of Vasoseal ES ®:The Experience of Skaggs Community Health Center", Cathlabdigest. com, Sep. 1, 2004, 2 pages, vol. 12, Issue 9.

Lomis et al., "Refractory Abdominal-Cutaneous Fistulas or Leaks: Percutaneous Management with a Collagen Plug," Journal of the American College of Surgeons, May 2000, pp. 588-592, vol. 190, No. 5.

McLean et al., "Enterocutaneous Fistulae: Interventional Radiologic Management," AJR:138, Apr. 1982, pp. 615-619.

Medeiros et al., "Treatment of Postoperative Enterocutaneous Fistulas By High-Pressure Vacuum with a Normal Oral Diet," Digestive Surgery, 2004, pp. 401-405, vol. 21.

O'Connor et al., "Efficacy of Anal Fistula Plug in Closure of Crohn's Anorectal Fistulas," Diseases of the Colon & Rectum, Dis Colon Rectum, Oct. 2006, pp. 1569-1573, vol. 49, No. 10.

Paul et al., "Bronchopleural Fistula Repair During Clagett Closure Utilizing a Collagen Matrix Plug," Ann. Thorac. Surg., 2007, pp. 1519-1521, vol. 83.

1st Examination Report for Canadian Patent Application No. 2,720,206, dated May 19, 2015, 3 pages.

Sutra, "Fistula in ano," Way2Ayurveda, www.way2ayurveda.com/fistulainano/index.html, printed Mar. 20, 2008, 3 pages, online publication.

Von Koperen et al., "Anal Fistula Plug for Closure of Difficult Anorectal Fistula: A Prospective Study," Diseases of the Colon & Rectum, Dis Colon Rectum, Aug. 2007, 5 pages, vol. 50, No. 8.

Wexner et al., "Practice Parameters for Treatment of Fistula-in-Ano-Supporting Documentation," ASCRS Standards Practice Task Force, Dis Colon Rectum, Dec. 1996, pp. 1363-1372, vol. 39, No. 12.

Zagrodnik II, "Fistula-in-Ano," General Surgery—Colorectal, Mar. 12, 2007, 15 pages.

\* cited by examiner

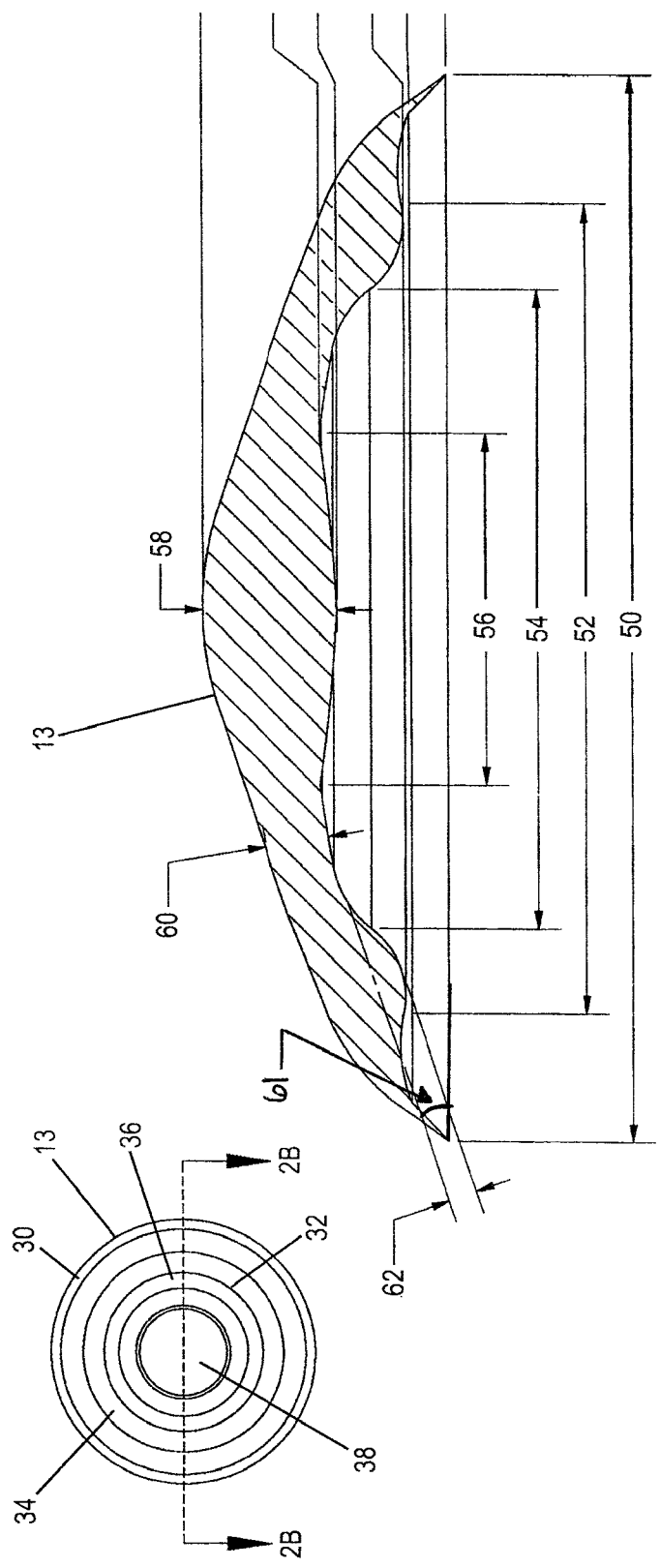

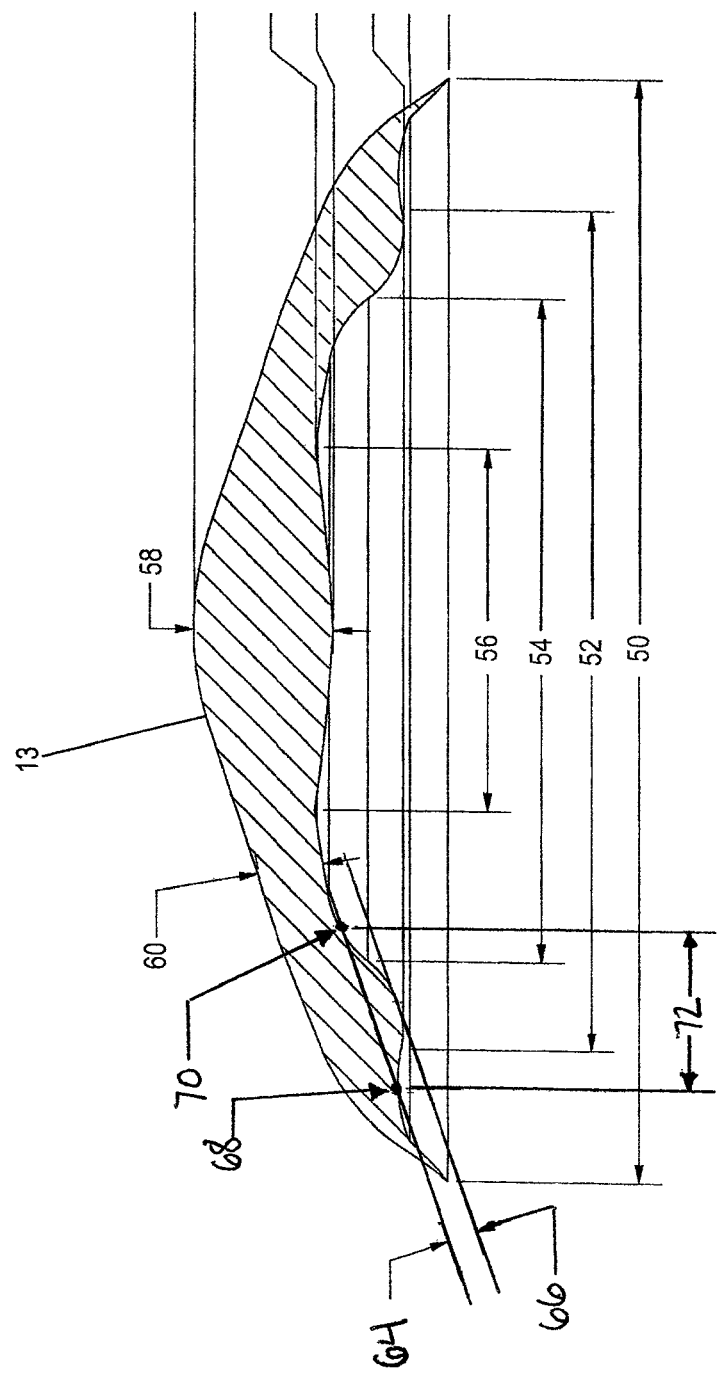

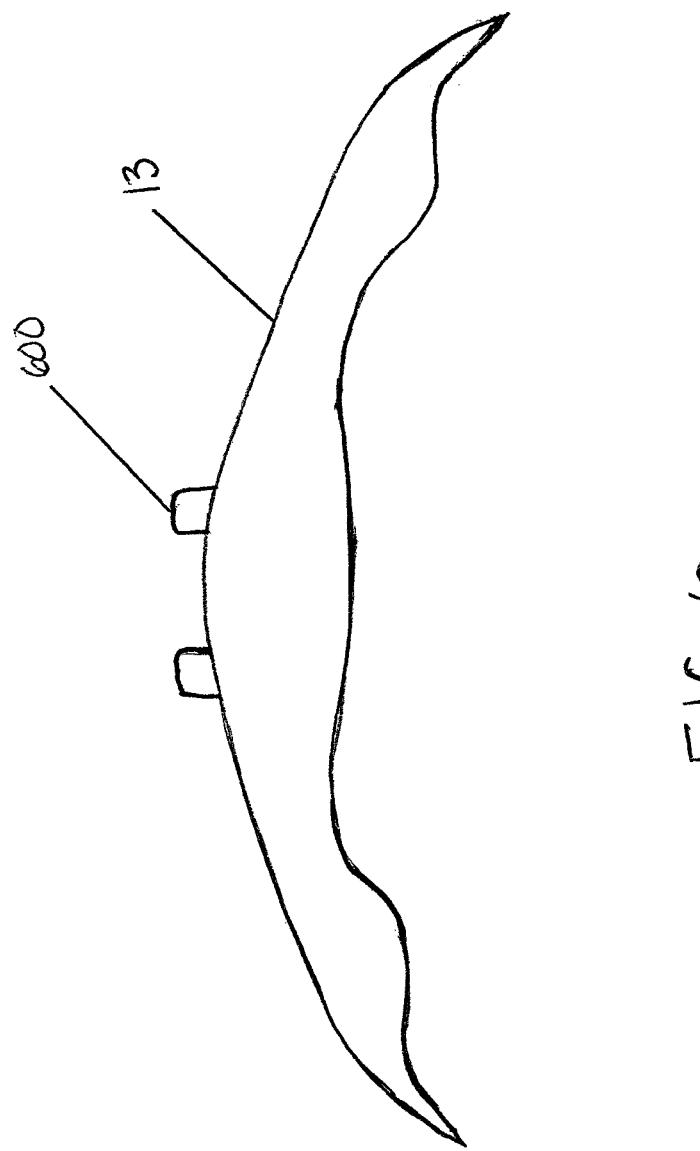

FISTULA TREATMENT DEVICES AND METHODS

CROSS-REFERENCE TO RELATED APPLICATION

This application claims priority under 35 U.S.C. §119(e) to U.S. Provisional Ser. No. 61/498,449, filed Jun. 17, 2011, which is hereby incorporated by reference in its entirety.

TECHNICAL FIELD

The present invention relates to medical apparatus and methods. More specifically, the present invention relates to implantable devices for closing fistulas and methods of using such devices.

BACKGROUND

Fistulas are a major cause of morbidity and mortality, as there are over one hundred thousand cases of pathologic fistulas a year, which account for over ten thousand deaths. They cost the healthcare system billions of dollars each year to treat.

Fistulas are tissue-lined connections between body cavities and hollow organs or between such cavities or organs and the surface of the body. The fistula tract includes a void in the soft tissues extending from a primary fistula opening to a blind ending or leading to one or more secondary fistula openings. Fistulas frequently develop as a consequence of infections or accompany abscess formations. Although some fistulas are purposely created for therapeutic purposes such as tracheostomy tracts, gastric feeding tube tracts, or arteriovenous fistulas for dialysis access, pathological fistulas are abnormal tracts that typically occur either congenitally or form after surgery, surgery-related complications, or trauma. They are most often open tracts that have epithelialized, endothelialized, or mucosalized.

Fistulas can form between almost any two-organ systems, or multiple organs, or between different locations of the same organ. For example, they may occur between internal organs and skin (enterocutaneous fistulas, gastrocutaneous fistulas, anal fistulas, rectovaginal fistulas, colocutaneous fistulas, vesiclocutaneous fistulas, intestinocutaneous fistulas, tracheocutaneous fistulas, bronchocutaneous fistulas, etc.) or between internal organs themselves (tracheal-esophageal fistulas, gastrointestinal fistulas, colovesicular fistulas, palatal fistulas, etc.). Anal or anorectal fistulas connect the anus and the rectum, and tend to be relatively short. Fistulas may also form between blood vessels such as arteriovenous fistulas.

Although fistulas may form in many locations in the body, they are almost universally highly morbid to patients and difficult for clinicians to treat. Some treatment options may include surgery, while other treatment options may include implantable devices designed to aid in the closure of the fistula. These devices, however, may cause adverse immunological reactions in patients, may allow leakage of fluid around them, or may result in contamination of the fistula tract. There is a need in the art for an implantable device for closing a fistula that reduces the chance of adverse immunological reactions, and the leakage of fluid through the fistula tract, and that has a reduced likelihood of contaminating the fistula tract during use.

SUMMARY

Disclosed herein are implantable fistula closure devices and related kits and methods, especially for use in the treatment of anorectal fistulas. In some embodiments, the anorectal fistula treatment device may comprise a disc-shaped distal anchor comprising a concave side and a convex side, an outer edge region, an inner sealing region protruding from the concave side, and an attachment region configured for attachment to a connecting member, wherein the inner sealing region has a greater thickness than at least a portion of the attachment region, and wherein the outer edge region is oriented at an acute angle to the inner sealing region. The distal anchor of the anorectal fistula treatment may have a tapered edge and the outer edge region and inner sealing region may be configured to form separate seals against tissue about a distal opening. The distal anchor of the anorectal treatment device may have a diameter in a range of about 0.6" to about 0.9". Additionally, the outer edge region of the distal anchor may comprise an average thickness that is in a range of about 0.005" and 0.03" and/or that is less than 10% of an outer diameter of the distal anchor. In some embodiments, the outer edge region may comprise an average thickness that is between about 3% and about 5% of the outer diameter of the anchor. The outer edge region may also comprise a width that is in a range of about 0.01" and 0.3" and/or is within a range of about 5% and 45% of an outer diameter of the distal anchor. In some embodiments, the outer edge region may comprise a width that is in a range of about 15% and 30% of an outer diameter of the distal anchor. The inner sealing region of the anorectal fistula treatment device may comprise an average thickness that is in a range of about 0.03" and about 0.09" and/or is less than about 25% of an outer diameter of the distal anchor. In some embodiments, the average thickness of the inner sealing region may be between about 5% and about 10% of an outer diameter of the distal anchor. The inner sealing region of anorectal fistula treatment device may also comprise a width that is between about 0.05" and 0.35" and/or within a range of about 5% and 45% of an outer diameter of the distal anchor. In some embodiments, the width of the inner sealing region may be between about 5% and 25% of an outer diameter of the distal anchor. The attachment region of the anorectal fistula treatment device may comprise an average thickness that is in a range of about 0.08" and 0.15" and/or is at least 30% of an outer diameter of the distal anchor. The attachment region may comprise a width that is within a range of about 0.15" and 0.35" and/or is within a range of about 15% and about 60% of an outer diameter of the distal anchor. In some embodiments, the width of the attachment region of the anorectal fistula treatment device may be within a range of about 25% and 40% of an outer diameter of the distal anchor. Additionally, the anorectal fistula device may comprise an inner sealing region comprising concentric outer and inner edges, and the distal anchor may further comprise a radius of curvature, measured radially between the inner edges of the inner sealing region, that may be in a range of about 0.12" and 0.75" and/or within a range of about 20% and 85% of an outer diameter of the distal anchor. In some embodiments, the radius of curvature, measured radially between the inner edges of the inner sealing region, may be within a range of about 35% and 55% of an outer diameter of the distal anchor.

The anorectal fistula treatment device may comprise a connecting member attached to the attachment region of the distal anchor and a tubular member. In some embodiments the connecting member may be threaded through the tubular member. The distal anchor of the anorectal fistula treatment device may comprise a disc of a first material and the attachment region may comprise a second material that is different from the first material. Additionally, the attachment region may comprise at least one layer member having a thickness that is less than the thickness of the attachment region. In some embodiments, the layer member may be comprised of mesh. The distal anchor may comprise at least one layer member with at least one hole. In some embodiments, the layer member may be adhered to the distal anchor. In other embodiments, the layer member may be embedded within the distal anchor. The connecting member of the anorectal fistula treatment device may be coupled to the layer member creating contact between the members. The contact between the connecting member and the layer member may be embedded within the distal anchor or it may be on an external surface of the distal anchor. In some embodiments, the distal anchor may further comprise tactile indicium on the convex side of the anchor. The tactile indicium may comprise one or more raise nodules and/or one or more indentations.

In any embodiment the anorectal fistula treatment device may comprise a disc-shaped distal anchor comprising a concave side and a convex side, the concave side comprising an outer edge region, an inner sealing region, an attachment region configured for attachment to a connecting member, and an intermediate region concentrically located between the inner sealing region and the attachment region. The attachment region may have a greater thickness than the intermediate region and the inner sealing region may have a greater thickness than the outer edge region and the intermediate region. The cross-sectional shape of the inner sealing region and the attachment region may be circular, triangular, ellipsoidal, or rectangular, among other shapes. In some embodiments, the inner sealing region may be equidistant from the outer edge region and the attachment region. In other embodiments, the distance between the inner sealing region and the attachment region may be either smaller or larger than the distance between the inner sealing region and the outer edge region. In some instances, the outer edge region of the distal anchor may comprise a proximal ring and a distal ring. The distal ring may be disposed in a first plane. Additionally, the inner sealing region may comprise concentric outer and inner edges and a ring, formed by a surface at a region of greatest thickness between the edges of the inner sealing region, may be disposed in a second plane. The first and second planes may be parallel to each other and the second plane may be located between the first plane and the attachment region. In some instances, the outer edge region may comprise concentric outer and inner edges and the outer edge may be disposed in a first plane. Additionally, in those instances, the angle formed between the first plane and an inner surface of the outer edge region may be less than or equal to 45 degrees. In various embodiments, the inner sealing region may comprise concentric outer and inner edges and a ring located at a midpoint between the edges of the inner sealing region which may protrude from the concave side of the distal anchor. Additionally, the outer edge region may comprise concentric outer and inner edges and the distal anchor may further comprise a radius of curvature, measured radially between the inner and outer edges of the outer edge region, which may be in a range of about 0.03" and 0.15". In some embodiments, the radius of curvature, measured radially between the inner and outer edges of the outer edge region, may be in a range of about 5% and 15% of an outer diameter of the distal anchor. In some embodiments, the outer edge region may comprise concentric outer and inner edges and the distal anchor may further comprise a first radius of curvature, measured radially between the inner and outer edges of the outer edge region. Additionally, the inner sealing region may comprise concentric outer and inner edges and the distal anchor may further comprise a second radius of curvature, measured radially between the edges of the inner sealing region. In some embodiments, the first radius of curvature may be in a range of about 10% and about 65% of the second radius of curvature. In some variations, the first radius of curvature may be in a range of about 15% and about 35% of the second radius of curvature.

While multiple embodiments are disclosed, still other embodiments of fistula treatment devices, kits and methods will become apparent to those skilled in the art from the following Detailed Description. As will be realized, the devices, kits and methods are capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2A is a top view of an anchor of the fistula closure device of FIG. 1, and FIG. 2B is a cross-sectional view of the anchor of FIG. 2A, taken along line 2B-2B. FIG. 2C is an additional cross-sectional view of the anchor of FIG. 2A, showing additional geometric measurements.

FIG. 6 depicts an anchor of a fistula closure device with tactile indicia.

DETAILED DESCRIPTION

Fistula tracts can be nonlinear or curvilinear and contain cavities of varying sizes at different intervals within the tract. Fistulas may also comprise multiple interconnected or branching passages. An implantable fistula closure device disclosed herein may employ advantageous design, configuration techniques and attributes to accommodate such constraints and may be used, for example, in the treatment of anorectal fistulas.

Figure 1:
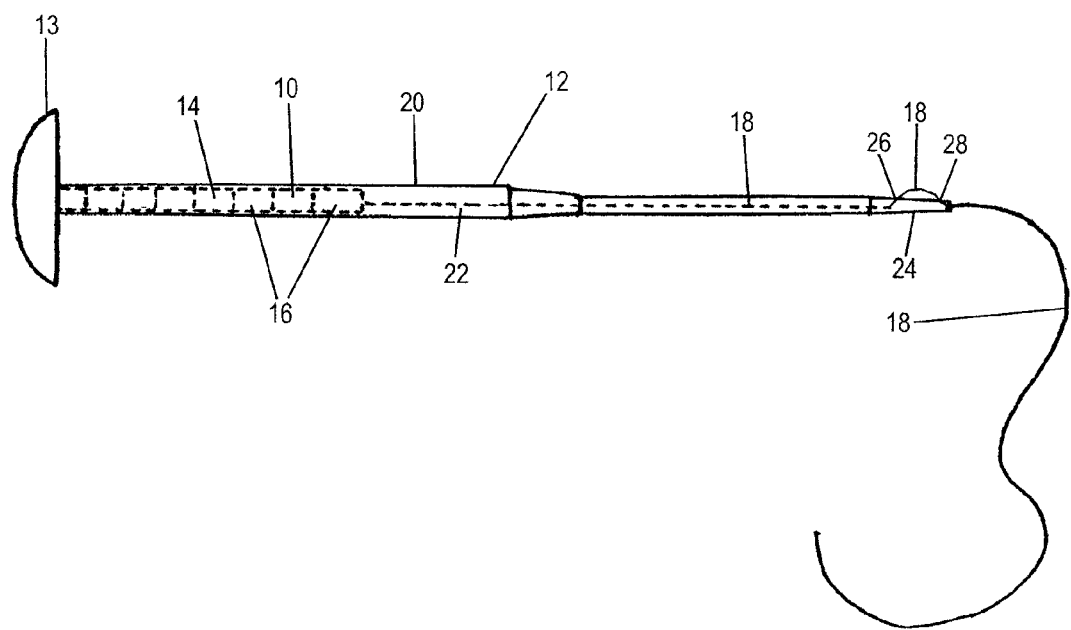
FIG. 1 is an illustrative side view of an embodiment of an implantable fistula closure device and its delivery device.

Referring to FIG. 1, an implantable fistula closure device 10 and its delivery device 12 are depicted. As shown there, the fistula closure device 10 includes a sealing member or distal anchor 13 and a segmented expandable body 14 formed of a plurality of individual expandable bodies or members 16 that are coupled together by a connecting member 18, such as a string or suture. The members 16 may be coupled together in an immediately adjacent abutting fashion (as shown) or in a spaced-apart fashion, and may be configured to slide between the two configurations. Upon insertion of the device 10 into a fistula tract with the expandable members 16 in a collapsed or compressed state, the expandable members 16 may, upon exposure to body heat or moisture, be allowed to soften and/or expand to fill the portion of the fistula tract in which each expandable member 16 is located. It should be noted that the collapsed or compressed state may allow for convenient insertion of the device 10 into the fistula tract. Additionally, the segmented nature of the body 14 of the device 10 or, and in some further variations, the fact that the device's body 14 is formed of a plurality of individual members 16, may allow the body 14 to be more easily bent and placed in, and to more readily conform to, the tortuous and diametrically varying configuration of a fistula tract when expanded within the fistula tract. Thus, once the body 14 is allowed to expand within the fistula tract, the device generally completely fills the fistula tract. It should be appreciated that the expandable members 16 may be designed to radially expand to various final diameters depending on the size, shape and characteristics of the fistula. In some embodiments, the expandable members 16 may expand very little such that the difference between their original and final diameters is negligible. In other embodiments, the expandable members 16 may increase more considerably. Additionally, if desired, expandable members 16 with different expansion characteristics may be utilized in one fistula closure device 10. Designing a fistula closure device 10 with diverse expandable members may help to better accommodate fistulas with changing diameters.

As shown in FIG. 1, the delivery device 12 may comprise a catheter or sheath 20 having a lumen 22 into which the fistula closure device 10 is loaded. During use, the loaded catheter or sheath 20 may be inserted into a fistula tract (e.g., an anorectal fistula tract), and the sealing member or anchor 13 may be positioned adjacent a distal opening of the fistula tract. Next, the loaded catheter or sheath 20 may be withdrawn from about the device body 14 to leave the device body 14 within the tract. The device body 14 may then expand to fill and occlude the tract.

In some embodiments, the delivery device 12 may comprise two or more catheters, cannulas or sheaths with lumens of different diameters. For example, the first catheter may have a lumen large enough to accommodate the connecting member 18. The first catheter may also comprise a tapered proximal end which may enhance the ease of movement through a fistula. The second catheter may comprise a lumen large enough to house the expandable members 16 and permit the second catheter to slide longitudinally over the first catheter when placing the expandable members 16 within a fistula tract. In some variations, the two catheters may be made from the same material. In other variations, the two catheters may be made from materials with different properties to aid in insertion, for example, materials with different stiffnesses. Additionally, the proximal end of the first catheter may comprise a resistance member or lock to resist or prevent the second catheter from sliding completely over the first catheter. In some embodiments, the resistance member or lock may also prevent inadvertent separation of the connecting member 18 from the delivery device 12. The lock may comprise any feature that prevents the separation of the first catheter from the second catheter, including but not limited to, a ring of greater diameter than the lumen of the second catheter, tabs extending radially at the proximal end of the first catheter, or apertures through which the connecting member 18 is looped, as shown in FIG. 1.

In certain embodiments, when the body 14 expands to fill the fistula tract, the device may generally stop fluid flow through the fistula tract. The time to closure and the necessity for surgery may be reduced (e.g., significantly) by preventing or reducing bodily fluids that originate at the distal end of the tract from passing through the fistula tract and, in some embodiments, also by reducing the amount or rate of flow through the fistula tract for body fluids originating in the tract itself. In certain embodiments, the fistula closure devices disclosed herein may reduce or eliminate the passage of fluids through a tract while also providing a matrix that promotes tissue growth.

While a segmented body 14 has been described, certain embodiments of tissue treatment devices may comprise a non-segmented body (i.e., a body that is a continuous, single-piece body as opposed to being formed from multiple bodies 16).

FIG. 2A shows a top view of the anchor 13, and FIG. 2B shows a cross-sectional view taken along line 2B-2B. As shown in FIGS. 2A and 2B (and in conjunction with FIG. 1), the anchor 13 is in the form of a concave resilient intestinal anchor that is configured to form a double seal against the tissue surface surrounding the distal opening of a fistula, such as an anorectal fistula. The seal formed by the anchor 13 may entirely block the distal opening or entry—for example, the anchor 13 may form a seal completely around the perimeter of the distal opening. In some cases, the anchor 13 may comprise one or more substantially impermeable or non-porous materials and may be substantially impermeable or non-porous. In certain embodiments, the anchor 13 may have a water vapor transmission rate (WVTR) of less than about 6000 g/m$^2$/24 hr (e.g., less than about 5000 g/m$^2$/24 hr, less than about 3000 g/m$^2$/24 hr, less than about 2000 g/m$^2$/24 hr, less than about 1000 g/m$^2$/24 hr, less than about 500 g/m$^2$/24 hr, less than about 250 g/m$^2$/24 hr, less than about 100 g/m$^2$/24 hr, less than about 50 g/m$^2$/24 hr, less than about 25 g/m$^2$/24 hr, less than about 15 g/m$^2$/24 hr, less than about 10 g/m$^2$/24 hr). Additionally, a hermetic seal may be formed in some embodiments.

In some embodiments, the anchor may be secured in place, which may improve the seal around the fistula opening. In some cases, a proximal clip at the end of the device 10 may be used to apply tension to the connecting member and the anchor, which may enhance the seal formed by the anchor and/or further secure the device 10 in the tract. In some variations, the anchor 13 may comprise one or more securing apertures that may permit the attachment of the anchor 13 to the skin or a bandage surrounding the dermal fistula opening. The securing apertures may be spaced around the periphery of the anchor. Any suitable number of apertures having any appropriate size may be used. In these variations, the anchor may be stitched in place using any suitable medical thread, including, but not limited, to absorbable thread and thread coated with antimicrobial substances. In other examples, the anchor may comprise adhesive on its proximal side that contacts the skin surrounding the fistula and resists movement. In some variations, the adhesive may be applied to the anchor during the manufacturing process, in which case the anchor may further comprise a release liner that is removable prior to use. In other variations, the adhesive may be applied by medical personnel prior to placing the device in a patient. In any embodiment, the anchor may comprise microneedles, barbs, hooks or any other suitable securing mechanism to fasten it to the tissue surface. The securing mechanisms may be distributed on the entire proximal surface, along the perimeter of the proximal surface, only inward from the inner sealing region or only between the inner sealing region and the outer edge region.

The anchor 13 may be configured not to actually enter the fistula tract itself. Rather, sealing by the anchor may generally occur around the fistula opening. The concave or curved nature of the anchor 13 may cause the middle region of the anchor 13 to be offset from, and distal to, the edge of the anchor 13. Additionally, in the case of, for example, an anorectal fistula, the concave or curved anchor 13 may contact a corresponding concave or curved tissue surface during use (i.e., the tissue surface around the distal fistula opening). It should be appreciated that while a concave or downward curved anchor is depicted, in some embodiments a flat or convex (upward curved) anchor may be used. The anchor 13 may provide multiple seals about the fistula opening. While most embodiments depict a dual or triple seal, any number of seals may be formed by adding additional sealing surfaces to the anchor. When a double seal is desired, the anchor 13 may be configured such that the outer edge region 30 and inner sealing region 32 seal the anchor around the fistula opening while the connecting member attachment region 38 is offset from the tissue surface. However, the anchor may be configured such that any combination of the outer edge region 30, the inner sealing region 32, and the connecting member attachment region 38 may act as seals. In some instances, it may be desirable for a triple seal to be formed around the fistula, in which case the anchor may form a seal at the outer edge region 30, inner sealing region 32, and connecting member attachment region 38. While the seals in FIG. 2A are depicted as full rings, it should be appreciated that the seals may be spiral shaped, interrupted rings, or any other shape that provides a sealing or healing benefit, for example, a tighter seal or enhanced breathability at the wound site. Additionally, while the anchor and seals are generally depicted as circular, the anchor itself, the outer edge region, the inner sealing region or the connecting member attachment region may be rectangular, oval, triangular, or any other suitable shape.

As shown in FIG. 2A, the anchor 13 comprises a relatively compliant outer edge region 30 and a beveled inner sealing region 32 having a first edge 34 and a second edge 36. The outer edge region 30 may be relatively flat or may form a concave transition from the inner sealing region 32. The two rings 30 and 32 may provide for a double seal during use that sits outside of the fistula tract. While the anchor 13 comprises a connecting member attachment region 38 (which, as shown, may be centrally located), in this case there is no hole or aperture through the anchor 13. The connecting member 18 (not shown in FIG. 1B) is attached to the connecting member attachment region 38 during use. In some cases, the connecting member 18 may be tensioned or may otherwise have a force applied to it. In certain embodiments, the connecting member 18 may elongate by more than about 0.4 mm/N of force applied thereto, and in some cases by up to about 5, 10, 15 or 20 mm.

Figure 8:
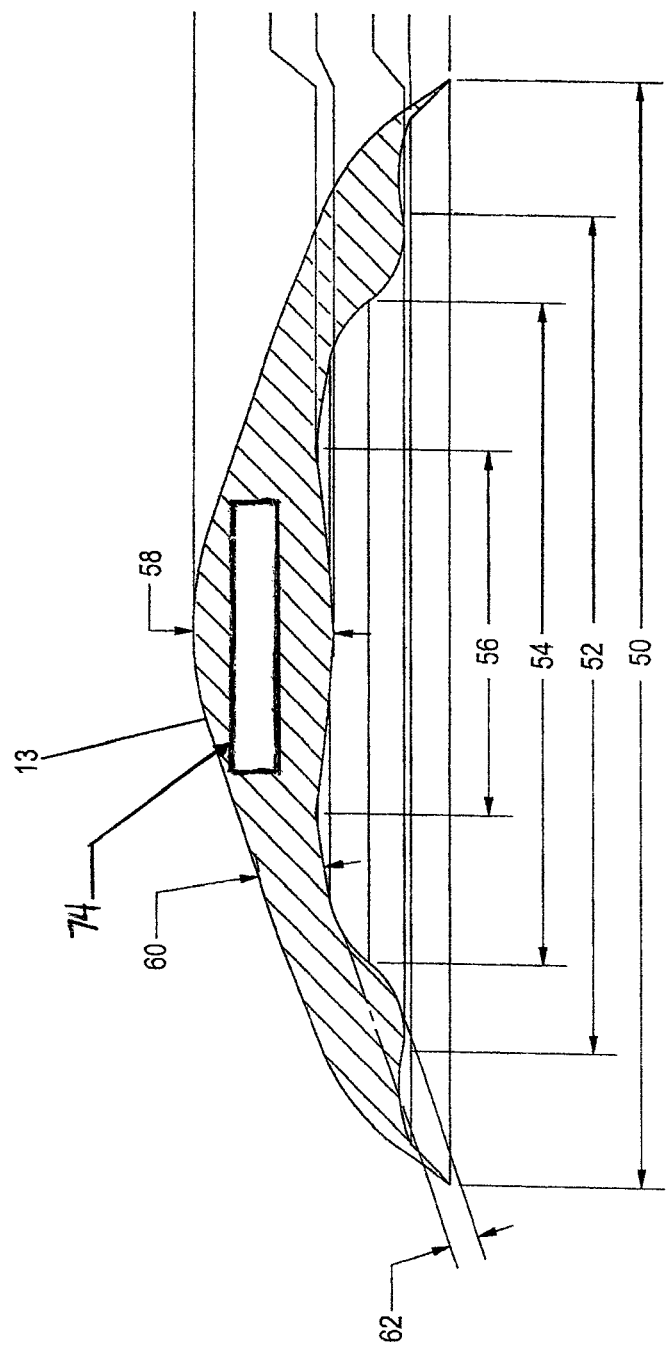
FIG. 8 depicts a cross-section of an anchor of a fistula closure device with an attachment region comprising layer members.

In some embodiments, the connecting member may be attached to the attachment region 38 prior to use. The attachment region 38 may be comprised of the same material as the remainder of the anchor 13, or, it may be comprised of one or more different materials. As depicted in FIGS. 2A and 8, the attachment region 38 may further be comprised of one or more layer members 74 optionally having a thickness that is less than the thickness of the attachment region 38 as a whole. For example, the attachment region may comprise three layer members, a base layer member and a top layer member made of the same material as the remainder of the anchor 13 and a middle layer member made of a different material, In another example, the middle layer member is sandwiched between two layer members formed from the upper and lower surfaces of the anchor 13. The middle layer member may be made of a material more suitable for attachment to the connecting member than the anchor 13, for example a mesh material or a solid disc made from a material of higher strength or rigidity than the anchor 13. The layer members may be coupled to the anchor in any suitable manner, including but not limited to, adhering the layer members to the anchor 13 or embedding the layer members within the anchor 13.

The connecting member may be coupled to the attachment region in any suitable manner, including but not limited to, using adhesives or weaving the connecting member through holes in the anchor or layer members. For example, in one embodiment, each end of the connecting member 18 may be inserted through an entrance hole in the base of the anchor 13 forming a loop on the proximal end, or underside, of the anchor 13. The two ends may then be threaded through entrance holes in a layer member and brought together to meet in parallel on the distal side of the layer member. The ends may then be inserted together through parallel exit holes in the layer member and anchor. The exit holes may be located in between (e.g. in the center of) the two entrance holes such that the connecting member forms two smaller loops on the distal side of the layer member. The loops formed on the layer member create contact between the connecting member 18 and the layer member. This contact may be on an internal surface of the distal anchor 13, for example, when the layer member is embedded within the distal anchor 13, or it may be on an external surface of the distal anchor 13. The ends of the connecting member 18 may then be threaded through the device body 14 and the delivery device 12. Furthermore, any number of connecting members may be coupled to the attachment region of an anchor. In some embodiments, more than one connecting member may be coupled to the attachment region to treat more than one fistula with one anchor, for example, to occlude branching or interconnected fistulas, or fistulas that may originate close to each other.

In another embodiment, the connecting member comprises two elements coupled together with, for example, a knot at one end. The opposite ends of the two elements may then be threaded through the layer member and the anchor 13 in the same manner as is discussed above forming loops on the proximal and distal sides of the anchor and layer member respectively. However, the connecting member elements may also be threaded through the layer member and anchor from the opposite direction (i.e. from the distal end of the layer member and anchor toward the proximal end) using two parallel holes in the layer member and base of the anchor 13. The two free ends of the elements of the connecting member 18 may then be threaded through the device body 14 and the delivery device 12, or they may be coupled together prior to threading (i.e. fused, adhered, etc.). The connecting member 18 may also be adhered to the layer member or to a surface of the anchor 13 using any suitable adhesive material.

The connecting member 18 may comprise any suitable medical thread or suture. In some examples, the medical thread may be coated with a drug-eluting compound or an antimicrobial substance. Additionally or alternatively, the thread may be impregnated with therapeutic agents that may include healing factors, antibiotics or other healing agents.

As shown in FIG. 6, the attachment region 38 may comprise tactile indicia on the convex side of the anchor. The tactile indicia may help a physician determine the proper placement of the anchor if visibility is low and may serve as a marker for further treatment. The tactile indicia may take any form or structure that allows for the determination of the location of the anchor 13 by touch. FIG. 6 is a cross-section of an anchor 13 with raised nodules 600. As shown in FIGS. 7A-7D, the tactile indicia can include, for example, raised or indented nodules 700, a cross pattern 702, grooves 704, a raised spiral 706, or any other raised on indented pattern. Additionally or alternatively, the anchor generally, or the attachment region specifically, may comprise a radio-opaque material or marker which may further assist a physician in determining proper placement of the anchor through visualization by X-ray, CT, or other imaging modalities.

Many different geometric features may affect the sealing properties of the distal anchor 13. The geometric variables that may determine the sealing nature of the distal anchor 13 may include, but are not limited to, the widths of the outer and inner sealing regions 30 and 32 as well as the attachment region 38, the height of the inner sealing region 62, the thickness of the outer edge region, the location of the inner sealing region 32 with respect to the outer edge region 30 and the attachment region 38, the cross-sectional shape of the inner sealing region 32 and the attachment region 38, the angle measured from the tissue of a patient to an inner surface of the outer edge region 30 and the radii of curvature at different locations on the anchor 13.

FIG. 2B depicts a cross-section of an embodiment of a dual-seal anchor 13 comprising outer edge region 30 providing a first seal, and inner sealing region 32 providing a second seal. The attachment region 38 may optionally act as a third sealing surface across its width (i.e. diameter) 56, or along its perimeter. The outer edge region 30 has an outer diameter 50, equal to the diameter of the anchor 13. The outer edge region has an inner diameter 52, which is also the diameter of the first edge of the inner sealing region 32. The width of the outer edge region 30 may be calculated by subtracting the diameter of the first edge of the inner sealing region 52 from the outer diameter of the outer edge region 50. The width of the inner sealing region 32 may be calculated by subtracting the diameter of the second edge of the inner sealing region 54 from the diameter of the first edge of the inner sealing region 52. The width of the attachment region 56 is the distance between the points on the anchor where the thickness of the anchor returns to the base thickness 60 on either side of the attachment region 38.

In some embodiments, the width of the outer edge region 30 is between about 0.01" and 0.45" and/or within a range of about 5% and about 60% of the outer diameter of the distal anchor 50 (e.g. between about 15% and about 30%). Additionally, in certain embodiments, the width of the inner sealing region may be between about 0.05" and 0.35" and/or within a range that is between about 5% and about 45% of the outer diameter of the distal anchor 50 (e.g. between about 5% and 25%). In any embodiment of the invention, the width of the attachment region 56 may be within a range that is between about 0.15" and about 0.35" (e.g. 0.247") and/or between about 15% and about 60% of the outer diameter of the anchor 13 (e.g. between about 25% and 40%).

The first and second diameters of the inner sealing region, 52 and 54 respectively, are measured with respect to the height of the inner sealing region 62. The inner sealing region may comprise a height 62 that protrudes from the concave side of the distal anchor 13. The height of the inner sealing region 62 is the maximum thickness of the inner sealing region (e.g. at the center of the ring) minus the base thickness of the anchor 60. As shown in FIG. 2C, in order to measure the height of the inner sealing region, a baseline 64 is drawn maintaining the base thickness of the anchor if it were formed without any additional projection from the inner sealing region 32. Likewise, a crest line 66 is drawn tangent to the peak (point of largest projection) of the inner sealing region 32. The baseline intersects the inner sealing region on its first edge creating a first edge intersection 68 and its second edge, creating a second edge intersection 70. The inner sealing region projection distance 72 is the distance between the first edge intersection 68 and the second edge intersection 70. The first edge diameter of the inner sealing region 52 is measured from the first edge intersection 68 plus ¼ the inner sealing region projection distance 72. The second edge diameter of the inner sealing region is measured from the second edge intersection 70 minus ¼ the inner sealing region projection distance 72.

In some embodiments, the average thickness of the inner sealing region 32 may be between about 0.03" and about 0.09" and/or may be less than 25% of the outer diameter of the distal anchor 50 (e.g. in a range of about 5% and about 10%). Additionally, the maximum thickness of the inner sealing region may be at a ring at the midpoint between the first edge of the inner sealing region 34 and the second edge of the inner sealing region 36. In other embodiments, the maximum thickness of the inner sealing region 34 may be located closer to one edge than to the other.

Figure 5:
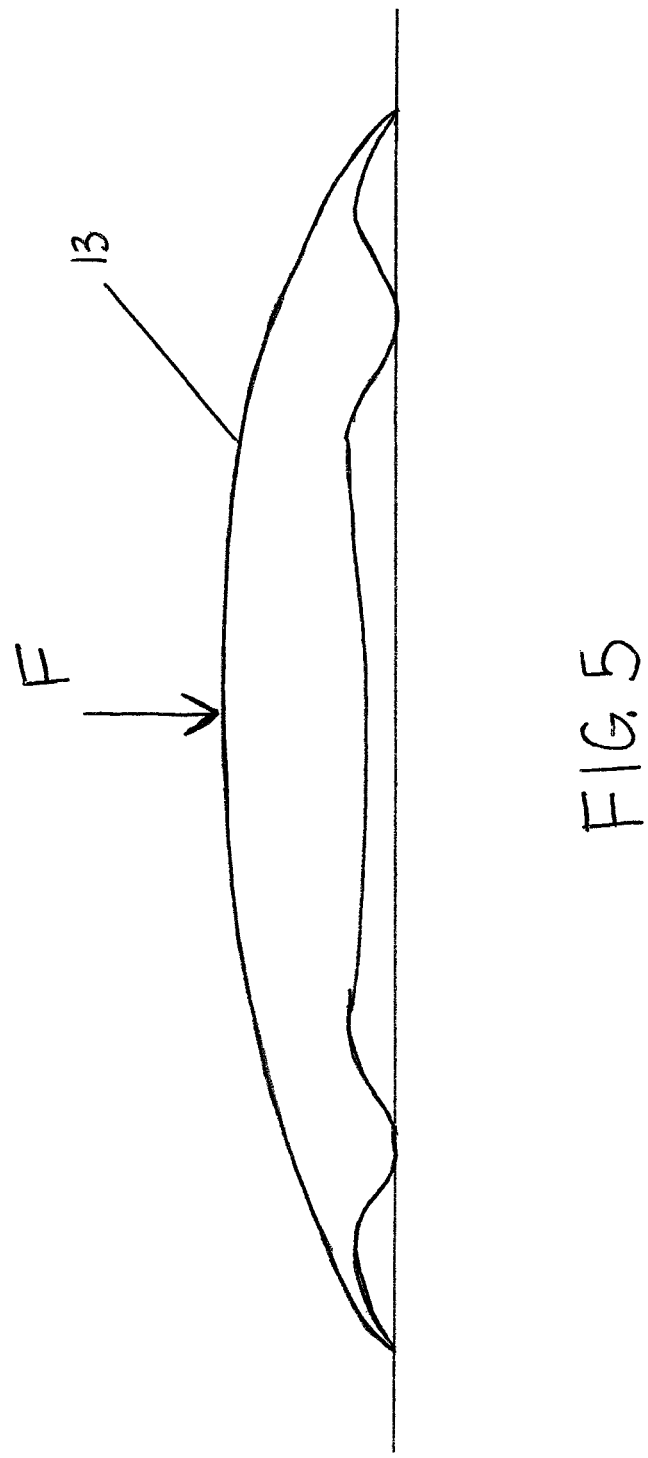
FIG. 5 is a cross-section of an anchor of a fistula closure device when a downward force is applied.
Figure 7A:
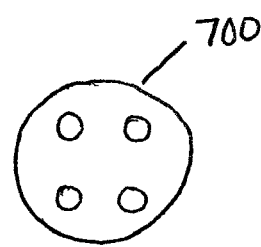
FIGS. 7A-D are illustrative top views of an anchor of a fistula closure device with different embodiments of tactile indicia.
Figure 7B:
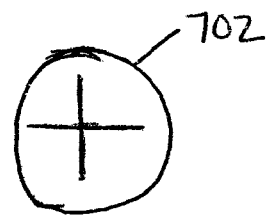
Figure 7C:
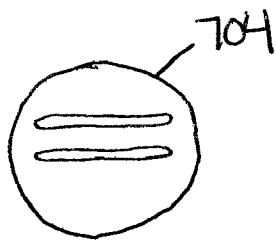
Figure 7D:
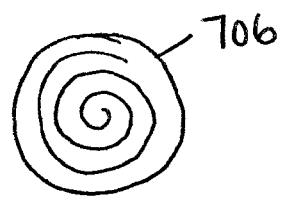

The outer edge region 30 may have concentric outer and inner edges between which the thickness of the outer edge region may vary. For example, in the embodiment shown in FIG. 2B, the outer edge region is tapered such that the thickness decreases radially outward from the inner edge of the outer edge region to the outer edge of the outer edge region. The taper of the outer edge region 30 may enhance its sealing properties when downward force is applied to the attachment region 38 by the connecting member 18, as shown in FIG. 5. The taper of the outer edge region may provide additional flexibility along the perimeter of the anchor such that when force is applied to the center of the anchor the outer edge does not feather or flip upwards. In some embodiments, the thickness of the outer edge region 30 may be in a range of about 0.005" to 0.03" and/or be less than about 10% of the outer diameter of the distal anchor 50 (e.g. between about 3% and about 5%). Furthermore, in certain embodiments, when the first edge of the outer edge region is placed within a first plane that is parallel to a second plane containing the apex of the inner sealing region, the second plane may be located between the first plane and the attachment region such that the cross-section of the anchor in its relaxed (no force applied) position has a semi-circular shape.

Varying the surface angle 61 formed by an inner surface of the outer edge region 30 and a plane disposed at the first edge of the outer edge region may affect the sealing properties of the anchor. Additionally, changing the outer radius of the curvature of the outer edge region 30, measured radially between the inner and outer edges of the outer edge region, may also impact the anchor's ability to seal effectively. These features create a concave surface between the outer edge region 30 and the inner sealing region 32 such that when a downward force is applied to the attachment region 38 during installation in a fistula, the apex of the inner sealing region 32 may seal the tissue surface while still allowing the outer edge region 30 to remain in contact with the tissue surface. An open space may be formed between the inner and outer edge of the outer edge region. The area of the open space may vary based upon the surface angle 61 and the radius of curvature of the outer edge region. In certain circumstances, a semi-circular space with a larger radius of curvature may be desirable to achieve the maximum sealing surface. In those circumstances, an anchor with a larger surface angle 61 and a shorter outer radius of curvature may be used. In some embodiments, the surface angle 61 may be between about 0 and 45 degrees and the outer radius of curvature of the outer edge region may be between about 0.03" and 0.15" and/or in a range that is about 5% and 15% of the outer diameter of the anchor 50.

Referring to FIG. 2B, in some embodiments, the diameter 50 may be about 0.6" to about 0.9" (e.g., 0.75"), the diameter 52 may be about 0.45" to about 0.7" (e.g., 0.57 inch), and the diameter 54 may be about 0.35" to about 0.65" (e.g., 0.45"). Furthermore, the connecting member attachment region 38 has a thickness 58 that may be, for example, from about 0.08" to about 0.15" (e.g., 0.095 inch). Additionally, the anchor 13 has a base thickness 60 that may be, for example, from about 0.03" to about 0.06" (e.g., 0.045 inch), and an inner sealing region height 62 that may be, for example, from about 0.001" to about 0.03" (e.g., 0.02").

While the connecting member attachment region 38 is depicted as generally circular, any appropriate shape and configuration may be used for a connecting member attachment region, including but not limited to semicircular, triangular, and ellipsoid. In some cases, the connecting member attachment region 38 may be relatively thick or pronounced. This may, for example, help to center the anchor 13 relative to a fistula opening. In some cases, the thickness of the connecting member attachment region 38 may be at least about 30% (e.g., at least about 40%, at least about 50%) of the outer diameter 50 of the anchor 13. In certain embodiments, the connecting member attachment region 38 may be designed not to be especially prominent (e.g. with a thickness within a range of about 5% to about 25% of the outer diameter 50). This may, for example, limit the likelihood of creating a pressure zone which can, in turn, lead to necrosis.

Other embodiments of anchors or sealing members having different configurations (e.g., sizes and/or shapes) may also be used. For example, FIGS. 3A-3M show side cross-sectional views of different embodiments of anchors or sealing members 300, 302, 304, 306, 308, 310, 312, 314, 316, 318, 320, 322 and 324, respectively. As shown there, anchor 300 has a relatively arched configuration, with a relatively steep transition from its inner sealing region to its outer edge region. Anchor 302 has a more gradual transition, and anchor 304 is relatively rounded in cross-section. Anchor 306 has much less of an arch than anchor 300 and may be used, for example, against a relatively flatter or less rounded surface.

The arched shape of the anchor may enhance its sealing ability by allowing both the outer and inner sealing regions to remain securely in contact with the tissue around a fistula when the anchor is placed. In some instances, the curve of the anchor also permits the outer and inner sealing regions to be in contact with the tissue surrounding the fistula, without also forcing the fistula opening to be in contact with the attachment region. The arch of the anchor may allow the attachment region to remain slightly displaced vertically from the surface of the opening of the fistula to prevent the anchor from interfering with the healing process, The arched shape of the anchors depicted in FIGS. 3A-3M may be characterized by an inner radius of curvature of the anchor, as measured radially between the inner edges of the second inner sealing region member. In some embodiments, the inner radius of curvature of the center section of the anchor, which characterizes the general arched structure, may be between about 0.12" and 0.75". Additionally or alternatively, the inner radius of curvature may be within a range of about 20% and about 85% of the outer diameter 50 of the anchor 13 (e.g. from about 35% to about 55%). Optionally, the outer radius of curvature of the outer edge region member may be between about 10% and about 65% of the inner radius of curvature (e.g. between about 15% and 35%).

Figure 3A:
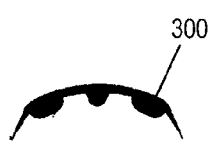
FIGS. 3A-3M are illustrative cross-sectional views of different embodiments of anchors of fistula closure devices.
Figure 3B:
Figure 3C:
Figure 3D:
Figure 3E:

FIGS. 3A-3E depict various cross-sectional embodiments of the anchor 13. These embodiments are generally smaller in diameter than the embodiments shown in FIGS. 3F-M. These embodiments may be appropriate for smaller fistulas or those with geometrical features that require a smaller distal anchor 13. The embodiments shown in FIGS. 3A-E as well as 3F-M vary in geometrical configuration, for example, with respect to the radii of curvature of the anchor as well as the surface angle formed. FIG. 3A depicts a smaller anchor 300 with a shorter inner radius of curvature but a large surface angle as compared to anchor 302. Anchor 302 is a smaller anchor with a flatter shape than anchors 300 and 304, as well as a smaller surface angle than anchor 300. Anchor 304 has a similar inner radius of curvature to FIG. 3A, but a smaller surface angle. Anchors 300, 302 and 306 show embodiments comprising inner sealing regions with fairly large maximum thicknesses and generally similar cross-sectional shapes, whereas anchor 308 depicts a smaller embodiment with both a less prominent inner sealing and attachment region.

While FIGS. 3A-3E depict embodiments with inner sealing regions characterized by fairly ellipsoidal cross-sections, it should be appreciated that any suitable cross-sectional shape can be used when designing both the inner sealing region and the attachment region. In some embodiments, the cross-section of the inner sealing region may be, for example, circular, triangular or rectangular. Additionally, the cross-sectional shape of the attachment region may also vary, and may include, but is not limited to, triangular, circular, ellipsoidal and rectangular cross-sections.

FIGS. 3F-3M more clearly illustrate examples of the various cross-sectional shapes of both the attachment region 38 as well as the inner sealing region 32. Anchors 310, 318, and 320 illustrate embodiments with fairly rectangular inner sealing region cross-sections, whereas anchor 322 is an example of an embodiment with a more triangular inner sealing region cross-section. Additionally, anchors 312, 314, 316 and 318 are examples of embodiments comprising triangular attachment region cross-sections. In contrast, anchors 322 and 324 illustrate embodiments comprising ellipsoidal attachment region cross-sections. It should be appreciated that the cross-sectional variations included in FIGS. 3A-3M are not exhaustive and are merely exemplary.

Figure 3F:
Figure 3G:
Figure 3H:
Figure 3I:
Figure 3J:
Figure 3K:
Figure 3L:
Figure 3M:

As depicted in FIG. 3F, the attachment region 38 of an anchor may have a significantly greater average thickness than an intermediate region between the attachment region and the inner sealing region. However, in other embodiments, for example the embodiment depicted by anchor 322, the average thickness of the attachment region may be similar to the thickness of the intermediate region between the attachment region and the inner sealing region. Furthermore, the distance between the first edge of the outer edge region and a ring located at the maximum thickness of the inner sealing region may vary. Additionally, the distance between a ring located at the maximum thickness of the inner sealing region and the attachment member region may also vary. For example, anchor 324 depicts an embodiment in which the maximum thickness of the inner sealing region is closer to the first edge of the outer edge region than to the attachment region, whereas, anchor 318 illustrates an embodiment in which a ring located at the maximum thickness of the inner sealing region is closer to the attachment region than to the outer edge region. In some embodiments, a ring located at the maximum thickness of the inner sealing region may be equidistant from the attachment region and the first edge of the outer edge region. Similar to FIGS. 3A-3E, FIGS. 3F-3M show embodiments with varying outer radii of curvature and surface angles. Anchor 324 is an example of an embodiment with a relatively short outer radius of curvature, as compared to anchor 310, for example. Additionally, FIGS. 3F-3M also illustrate embodiments comprising outer edge regions of various widths. Anchors 316 and 318 depict embodiments comprising outer edge regions with larger widths, whereas anchors 320, 322 and 324 show embodiments comprising outer edge regions with smaller widths.

Anchors may, of course, have any appropriate size, as indicated, for example, by anchor 308, which is relatively small. Anchor size may be determined, for example, by the dimensions of the fistula being treated. By contrast, anchor 310 is relatively large and has a more pointed connecting member attachment region, with a relatively steep transition from its inner sealing region member to its outer edge region member. Anchor 312 is also relatively large, but has a more gradual transition between its inner and outer edge region members. Anchor 314 has a similar configuration to anchor 310; however, the outer edge region member of anchor 314 is thinner than the outer edge region member of anchor 310. Anchor 316 is the largest anchor shown in FIGS. 3A-3M, and has a relatively smooth transition between its ring members, with the outer edge region member having a tapered edge. Anchor 318 has a similar configuration to anchor 316, but is smaller and has a thinner outer edge region member. Anchor 320 is relatively compact, with a relatively thick portion between its inner sealing region member and its connecting member attachment region. Anchor 322 also is relatively compact, and has an even thicker portion between its inner sealing region member and its connecting member attachment region. Finally, anchor member 324 has a relatively gradual and smooth curve with a rounded connecting member attachment region and an inner sealing region member that is relatively rounded in cross-section.

While certain embodiments of anchors or sealing members have been shown and described, other embodiments having different shapes and configurations may be used in a fistula closure device. Additionally, anchors or sealing members may be made of any suitable material or materials, including but not limited to polymers, such as polysiloxanes or silicones, polyethylene, polyurethane, fluoropolymers (e.g., polytetrafluoroethylene (PTFE), fluorinated ethylene propylene (FEP), perfluoroalkoxy (PFA)), metals and/or metal alloys. In some cases, anchors or sealing members may comprise at least one type of silicone polymer. In some variations, the anchor may further comprise a drug-eluting coating or material, or a material impregnated with a therapeutic agent that may include healing factors, antibiotics, or other healing agents.

Referring again to FIG. 1, the delivery device 12 further comprises a resistance member or lock 24 (e.g., a suture lock) that may be used to prevent inadvertent separation of the connecting member 18 from the delivery device 12. As shown, the connecting member may be routed through apertures 26 and 28 in the lock 24, such that the connecting member passes from the interior of the delivery device 12, to the exterior, and back into the interior again. While two apertures are shown, any appropriate number of apertures and any suitable connecting member routing configuration may be employed.

Figure 4A:
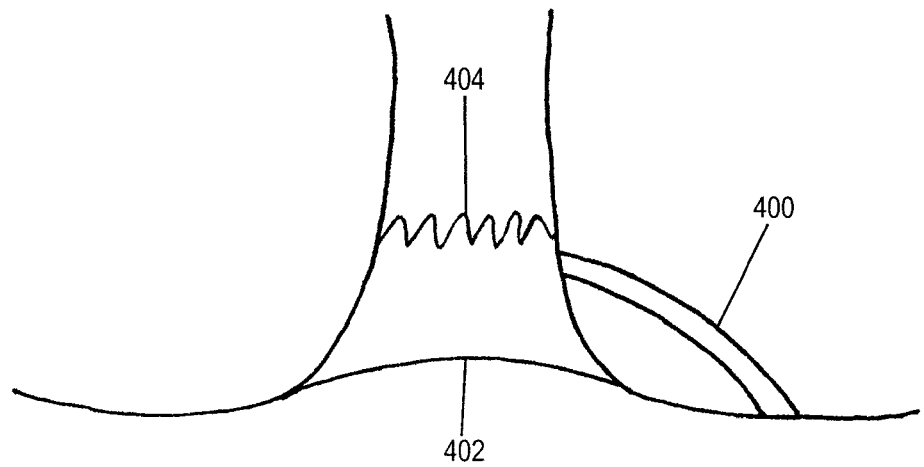
FIGS. 4A-4E depict an illustrative method of closing a fistula using a fistula closure device comprising an anchor.
Figure 4B:
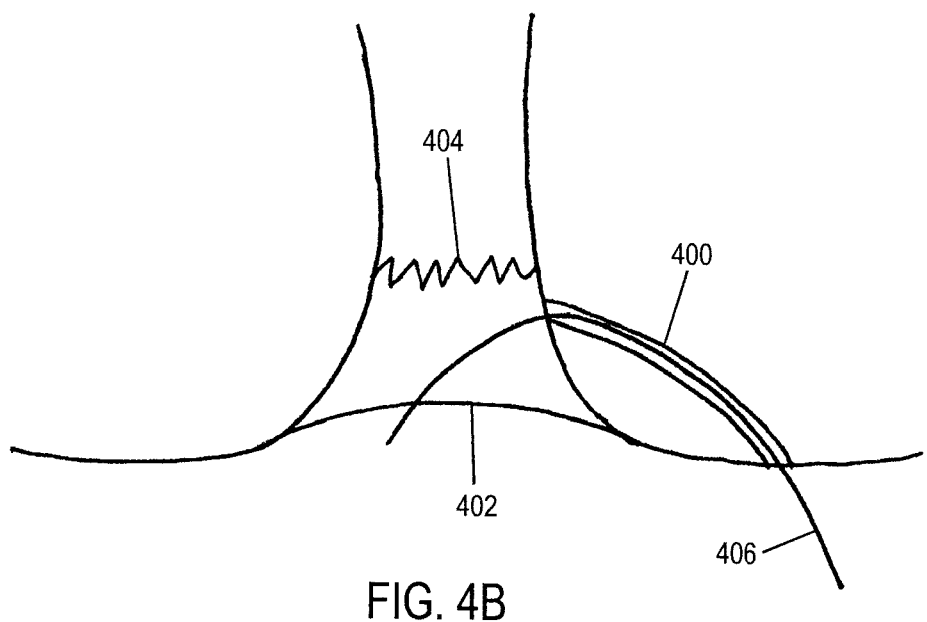
Figure 4C:
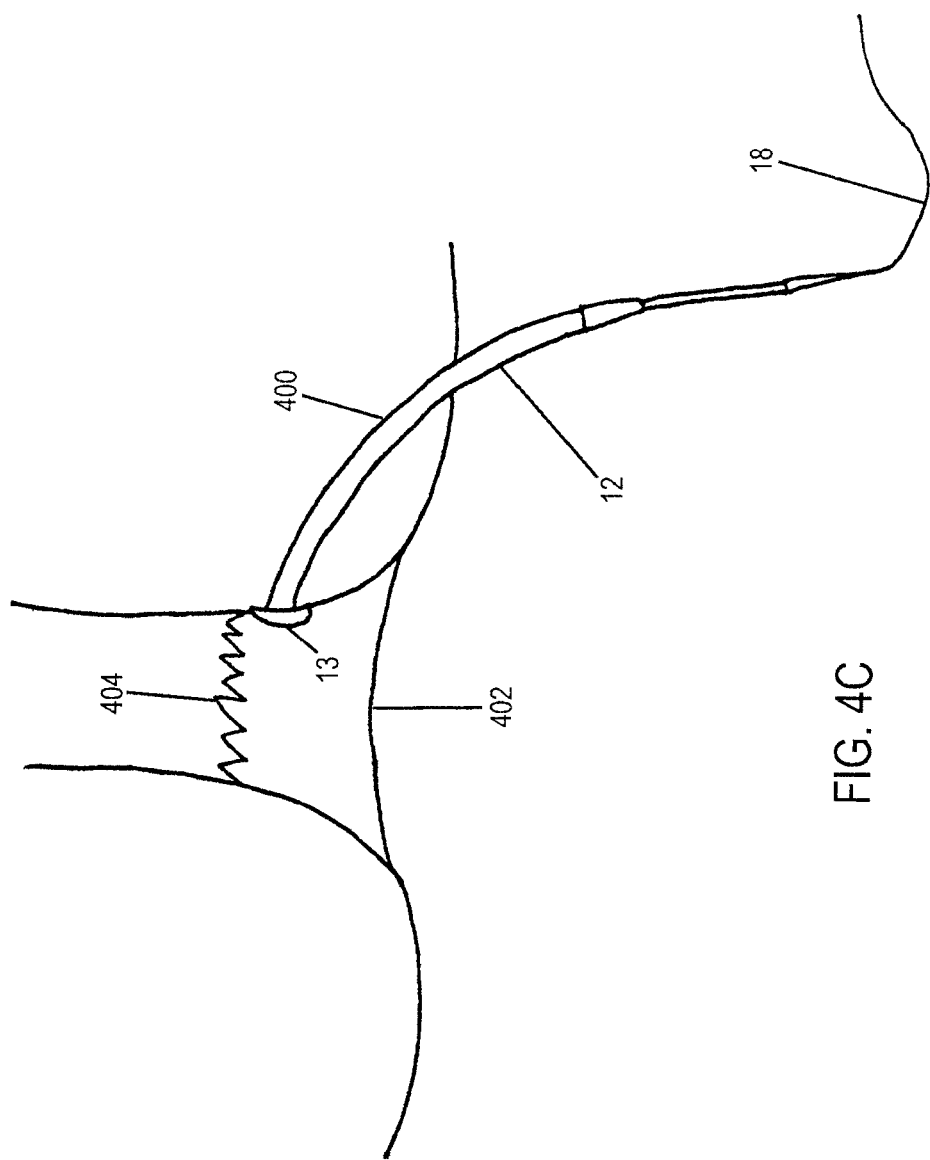
Figure 4D:
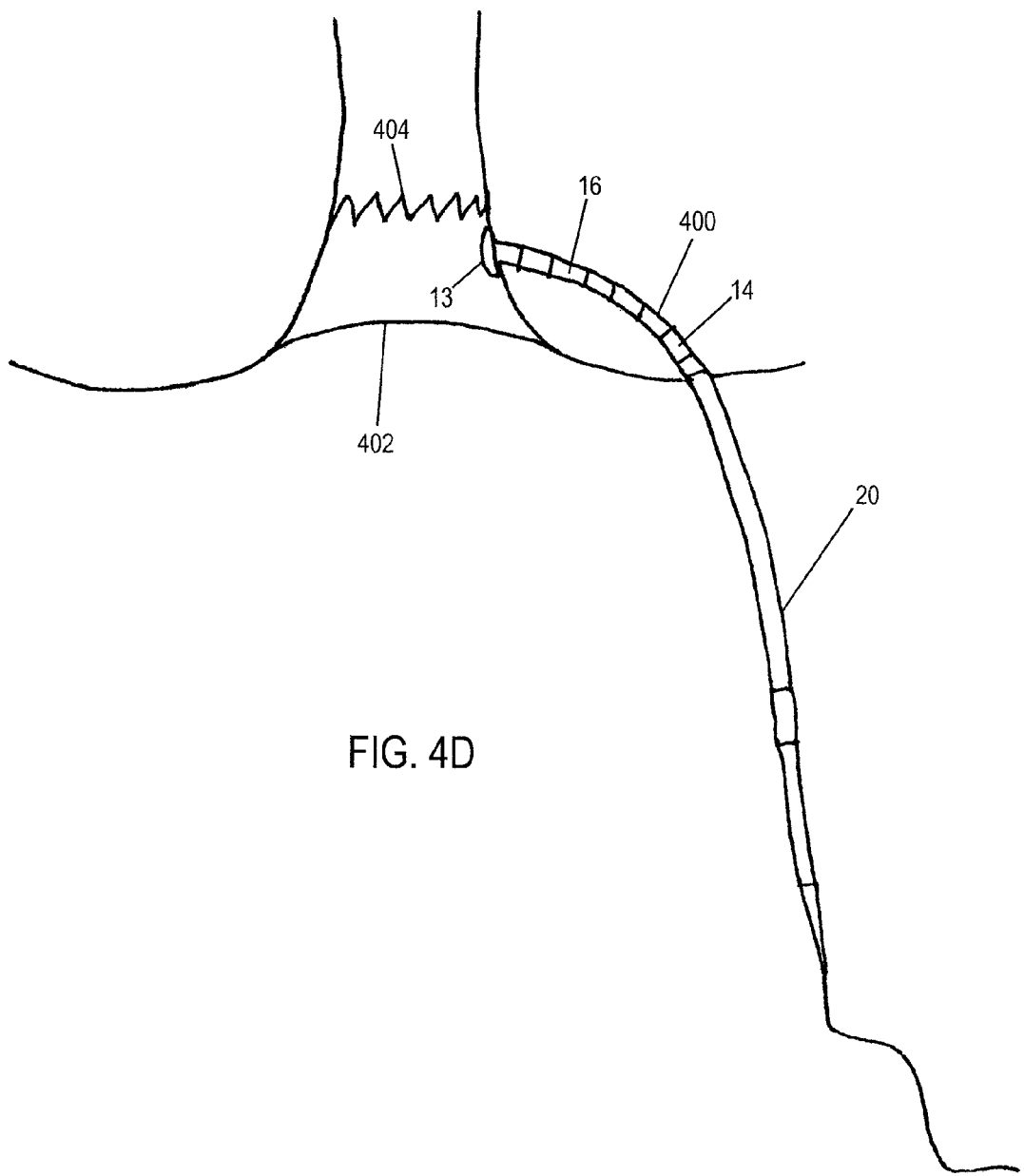
Figure 4E:
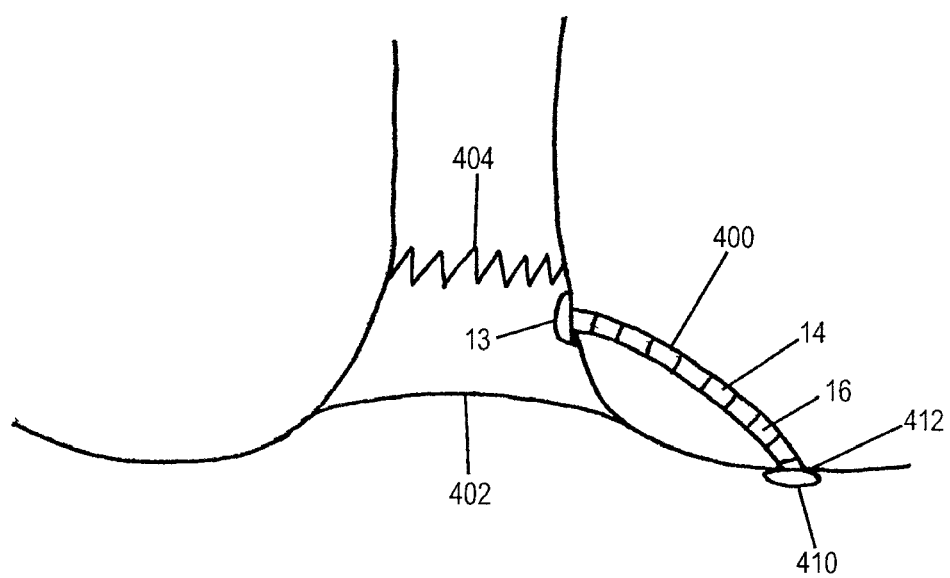

Any appropriate methods may be used to deliver or deploy the fistula treatment devices described herein. For example, FIGS. 4A-4E depict an embodiment of a method of delivering the fistula closure device 10 of FIG. 1 into an anorectal fistula tract 400. First, FIG. 4A shows the fistula tract 400, by the anus 402 and the dentate line 404. In FIG. 4B, a guidewire 406 has been passed through the fistula tract 400. Next, and referring to FIG. 4C, the delivery device 12 is used to deliver the fistula closure device 10 into the fistula tract 400. More specifically, the connecting member 18 may, for example, be attached to the guidewire 406, and the guidewire 406 may be used to pull the device 12 into the fistula tract 400. Referring now to FIG. 4D, the sheath 20 may be withdrawn to leave the device body 14 (including members 16) within the fistula tract 400. FIG. 4E shows the device 10 delivered to the target site, with the device body 14 positioned within the fistula tract 400, the anchor 13 positioned against a distal opening 408 of the fistula tract 400, and an optional proximal anchor 410 positioned against a proximal opening 412 of the fistula tract 400 (and, e.g., attached to the connecting member 18). While not shown here, in some cases the device 10 may alternatively or additionally be sutured in place at the location of the proximal opening 412 of the fistula tract 400. In some variations, an anoscope or other endoscope tool may be used during implantation. In some further variations, the anoscope or tool may comprise slots or apertures along its length to permit direct access to a fistula opening while displacing or supporting the surrounding tissue to improve visualization.

Advantageously, the design of the fistula closure device 10 and the delivery device 12 may allow the members 16 (e.g., collagen plugs) to be delivered into the fistula tract 400 without first being exposed to potentially substantial contamination prior to entering the fistula tract 400. Thus, contamination of the fistula tract 400 may be avoided or at least limited.

To perform the procedures described above, a kit may be provided that contains the fistula closure device 10 and the delivery device 12. In some cases, multiple different fistula closure devices (e.g., having sealing members 13 with different configurations) may be included in the kit. The fistula closure device 10 may be coupled to the delivery device 12 at the point-of-manufacture or at the point-of-use, and therefore may be provided in the kit either pre-attached or separate from the delivery device 12. The kit may also contain one or more other items, including but not limited to a guidewire (e.g. 0.038" guidewire), a peel-away sheath (e.g. 7 F, 8 F, 9 F, 10 F, or 12 F sheath), one or more syringes (e.g. 0.5 cc, 1 cc, 5 cc, and/or 10 cc syringes), saline or biocompatible fluid, contrast media, a scalpel, one or more free needles, and non-resorbable sutures (e.g. 3-0 or 4-0 nylon suture). A fistula tract dilator may also be provided in the kit. The contents of a kit may be provided in sterile packages. Instructions may be provided on or with the kit, or alternatively via the Internet or another indirect method, and may provide direction on how to employ the kit (e.g., outlining a deployment method such as one of those described herein).

While preferred embodiments of the present invention have been shown and described herein, it will be obvious to those skilled in the art that those examples are brought by way of example only. Numerous changes, variations, and substitutions will now occur to those skilled in the art without departing from the invention. It should be understood that various alternatives to the embodiments of the invention described herein may be employed in practicing the invention. It is intended that the following claims define the scope of the invention and that the methods and structures within the scope of these claims will be covered thereby.

What is claimed is:
1. An anorectal fistula treatment device, comprising:
a disc-shaped distal anchor, comprising:
a concave side;
a convex side;
an outer edge region, comprising a first ring along an outer edge of the distal anchor;
an inner sealing region protruding from the concave side and comprising a second ring concentrically disposed within the first ring;
a concave transition formed by the outer edge region and extending from the inner sealing region toward the outer edge of the distal anchor;
an attachment region protruding from a center of the concave side of the distal anchor and configured for attachment to a connecting member; and
an intermediate region between the inner sealing region and the attachment region, wherein the attachment region has a greater average thickness than the intermediate region;

wherein the inner sealing region has a greater thickness than at least a portion of the attachment region.

2. The anorectal fistula treatment device of claim 1, wherein the distal anchor has a tapered edge and wherein the outer edge region and inner sealing region are configured to form separate seals against tissue about a distal opening.

3. The anorectal fistula treatment device of claim 2, wherein the diameter of the distal anchor is in a range of about 0.6" to 0.9".

4. The anorectal fistula treatment device of claim 1, wherein the outer edge region comprises an average thickness that is less than 10% of an outer diameter of the distal anchor.

5. The anorectal fistula treatment device of claim 1, wherein the outer edge region comprises an average thickness that is in a range of about 3% and 5% of an outer diameter of the distal anchor.

6. The anorectal fistula treatment device of claim 1, wherein the outer edge region comprises an average thickness that is in a range of about 0.005" and 0.03".

7. The anorectal fistula treatment device of claim 1, wherein the outer edge region comprises a width that is in a range of about 5% and 60% of an outer diameter of the distal anchor.

8. The anorectal fistula treatment device of claim 1, wherein the outer edge region comprises a width that is in a range of about 15% and 30% of an outer diameter of the distal anchor.

9. The anorectal fistula treatment device of claim 1, wherein the outer edge region comprises a width that is in a range of about 0.01" and 0.45".

10. The anorectal fistula treatment device of claim 1, wherein the inner sealing region comprises an average thickness that is less than 25% of an outer diameter of the distal anchor.

11. The anorectal fistula treatment device of claim 1, wherein the inner sealing region comprises an average thickness that is in a range of about 5% and 10% of an outer diameter of the distal anchor.

12. The anorectal fistula treatment device of claim 1, wherein the inner sealing region comprises an average thickness that is in a range of about 0.03" and 0.09".

13. The anorectal fistula treatment device of claim 1, wherein the inner sealing region comprises a width that is in a range of about 5% and 45% of an outer diameter of the distal anchor.

14. The anorectal fistula treatment device of claim 1, wherein the inner sealing region comprises a width that is in a range of about 5% and 25% of an outer diameter of the distal anchor.

15. The anorectal fistula treatment device of claim 1, wherein the inner sealing region comprises a width that is in a range of about 0.05" and 0.35".

16. The anorectal fistula treatment device of claim 1, wherein the attachment region comprises an average thickness that is in a range of about 5% and 25% of an outer diameter of the distal anchor.

17. The anorectal fistula treatment device of claim 1, wherein the attachment region comprises an average thickness that is at least 30% of an outer diameter of the distal anchor.

18. The anorectal fistula treatment device of claim 1, wherein the attachment region comprises an average thickness that is in a range of about 0.08" and 0.15".

19. The anorectal fistula treatment device of claim 1, wherein the attachment region comprises a width that is in a range of about 15% and 60% of an outer diameter of the distal anchor.

20. The anorectal fistula treatment device of claim 1, wherein the attachment region comprises a width that is in a range of about 25% and 40% of an outer diameter of the distal anchor.

21. The anorectal fistula treatment device of claim 1, wherein the attachment region comprises a width that is in a range of about 0.15" and 0.35".

22. The anorectal fistula treatment device of claim 1, wherein the inner sealing region comprises concentric outer and inner edges, and wherein the distal anchor further comprises a radius of curvature, measured radially between the inner edges of the inner sealing region, that is in a range of about 20% and 85% of an outer diameter of the distal anchor.

23. The anorectal fistula treatment device of claim 1, wherein the inner sealing region comprises concentric outer and inner edges, and wherein the distal anchor further comprises a radius of curvature, measured radially between the inner edges of the inner sealing region, that is in a range of about 35% and 55% of an outer diameter of the distal anchor.

24. The anorectal fistula treatment device of claim 1, wherein the inner sealing region comprises concentric outer and inner edges, and wherein the distal anchor further comprises a radius of curvature, measured radially between the inner edges of the inner sealing region, that is in a range of about 0.12" and 0.75".

25. A disc-shaped distal anchor of an anorectal fistula treatment device, the disc-shaped distal anchor comprising:
   a concave side;
   a convex side;
   an outer edge region disposed along an outer edge of the distal anchor;
   an inner sealing region protruding from the concave side and disposed within the outer edge region;
   an attachment region disposed within the inner sealing region and configured for attachment to a connecting member; and
   at least one layer member coupled with the attachment region;
   wherein the at least one layer member comprises a middle layer member embedded within the attachment region; and
   wherein the middle layer member comprises a disc made of a first material that has at least one of a greater strength or a greater rigidity than that of a second material of which the disc-shaped distal anchor is made.

26. The disc-shaped distal anchor of claim 25, wherein the disc comprises a mesh material.

27. The disc-shaped distal anchor of claim 25, wherein the disc comprises a solid material.

28. The disc-shaped distal anchor of claim 25, wherein the middle layer member is sandwiched between two additional layer members formed from upper and lower surfaces of the disc-shaped distal anchor.

* * * * *